US010299918B2

(12) United States Patent
Tuval

(10) Patent No.: US 10,299,918 B2
(45) Date of Patent: May 28, 2019

(54) VENA-CAVAL DEVICE

(71) Applicant: MAGENTA MEDICAL LTD., Kadima (IL)

(72) Inventor: Yosi Tuval, Even Yehuda (IL)

(73) Assignee: MAGENTA MEDICAL LTD., Kadima (IL)

( * ) Notice: Subject to any disclaimer, the term of this patent is extended or adjusted under 35 U.S.C. 154(b) by 0 days.

(21) Appl. No.: 15/423,368

(22) Filed: Feb. 2, 2017

(65) Prior Publication Data

US 2017/0143483 A1 May 25, 2017

Related U.S. Application Data

(63) Continuation of application No. 14/405,144, filed as application No. PCT/IL2013/050495 on Jun. 6, 2013, now Pat. No. 9,597,205.

(60) Provisional application No. 61/656,244, filed on Jun. 6, 2012.

(51) Int. Cl.

| | |
|---|---|
| ***A61F 2/82*** | (2013.01) |
| ***A61F 2/24*** | (2006.01) |
| ***A61F 2/856*** | (2013.01) |
| *A61F 2/91* | (2013.01) |

(Continued)

(52) U.S. Cl.

CPC .............. *A61F 2/2418* (2013.01); *A61F 2/82* (2013.01); *A61F 2/856* (2013.01); *A61F 2/2436* (2013.01); *A61F 2/91* (2013.01); *A61F 2/966* (2013.01); *A61F 2002/821* (2013.01); *A61F 2002/8483* (2013.01); *A61F 2002/8486* (2013.01); *A61F 2230/005* (2013.01); *A61F 2230/0054* (2013.01); *A61F 2230/0067* (2013.01); *A61F 2250/006* (2013.01)

(58) Field of Classification Search

CPC .. A61F 2/2418; A61F 2/82; A61F 2230/0054; A61F 2230/0067

See application file for complete search history.

(56) References Cited

U.S. PATENT DOCUMENTS

| | | | |
|---|---|---|---|
| 4,919,647 | A | 4/1990 | Nash |
| 4,954,055 | A | 9/1990 | Raible et al. |
| 5,613,935 | A | 3/1997 | Jarvik |

(Continued)

FOREIGN PATENT DOCUMENTS

| | | |
|---|---|---|
| AU | 2013205145 | 5/2013 |
| JP | 2012505038 A | 3/2012 |

(Continued)

OTHER PUBLICATIONS

An Office Action dated Sep. 20, 2017, which issued during the prosecution of Chinese Patent Application No. 201380037335.4.

(Continued)

*Primary Examiner* — Dinah Baria
(74) *Attorney, Agent, or Firm* — Dorsey & Whitney LLP

(57) ABSTRACT

Apparatus and method are described including identifying a subject as suffering from a condition that causes the subject to have elevated central venous pressure. In response thereto, a device is placed inside the subject's vena cava such that an upstream end of the device is placed at a location upstream of junctions of the vena cava with all of the subject's renal veins. The device defines a passage through the device, at least a portion of the passage converging in a direction from an upstream end of the device to downstream end of the device. Other applications are also described.

9 Claims, 24 Drawing Sheets

(51) Int. Cl.

| | |
|---|---|
| *A61F 2/966* | (2013.01) |
| *A61F 2/848* | (2013.01) |

(56) References Cited

U.S. PATENT DOCUMENTS

| | | | |
|---|---|---|---|
| 5,713,730 | A | 2/1998 | Nose et al. |
| 5,749,855 | A | 5/1998 | Reitan |
| 5,772,693 | A | 6/1998 | Brownlee |
| 5,876,385 | A | 3/1999 | Ikari et al. |
| 5,964,694 | A | 10/1999 | Siess et al. |
| 6,086,527 | A | 7/2000 | Talpade |
| 6,135,729 | A | 10/2000 | Aber |
| 6,247,892 | B1 | 6/2001 | Kazatchkov et al. |
| 6,482,228 | B1 | 11/2002 | Norred |
| 6,533,716 | B1 | 3/2003 | Schmitz-Rode et al. |
| 6,592,567 | B1 | 7/2003 | Levin et al. |
| 6,616,624 | B1 | 9/2003 | Kieval |
| 6,884,210 | B2 | 4/2005 | Nose et al. |
| 7,004,925 | B2 | 2/2006 | Navia et al. |
| 7,144,364 | B2 | 12/2006 | Barbut et al. |
| 7,159,593 | B2 | 1/2007 | McCarthy et al. |
| 7,335,192 | B2 | 2/2008 | Keren et al. |
| 7,341,570 | B2 | 3/2008 | Keren et al. |
| 7,485,104 | B2 | 2/2009 | Kieval |
| 7,717,952 | B2 | 5/2010 | Case et al. |
| 7,744,642 | B2 | 6/2010 | Rittgers |
| 7,762,941 | B2 | 7/2010 | Jarvik |
| 7,766,853 | B2 | 8/2010 | Lane |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,914,503 | B2 | 3/2011 | Goodson et al. |
| 8,012,121 | B2 | 9/2011 | Goodson et al. |
| 8,079,948 | B2 | 12/2011 | Shifflette |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | McBride et al. |
| 8,449,443 | B2 | 5/2013 | Rodefeld et al. |
| 8,512,262 | B2 | 8/2013 | Gertner |
| 8,538,535 | B2 | 9/2013 | Gross et al. |
| 8,579,858 | B2 | 11/2013 | Reitan et al. |
| 8,617,239 | B2 | 12/2013 | Reitan |
| 8,734,331 | B2 | 5/2014 | Evans et al. |
| 8,734,508 | B2 | 5/2014 | Hastings et al. |
| 8,777,832 | B1 | 7/2014 | Wang et al. |
| 8,849,398 | B2 | 9/2014 | Evans |
| 9,028,216 | B2 | 5/2015 | Schumacher et al. |
| 9,138,518 | B2 | 9/2015 | Campbell et al. |
| 9,162,017 | B2 | 10/2015 | Evans et al. |
| 9,314,558 | B2 | 4/2016 | Er |
| 9,358,329 | B2 | 6/2016 | Fitzgerald et al. |
| 9,764,113 | B2 | 9/2017 | Tuval et al. |
| 10,039,874 | B2 | 8/2018 | Schwammenthal et al. |
| 2003/0055486 | A1 | 3/2003 | Adams et al. |
| 2004/0064090 | A1 | 4/2004 | Keren et al. |
| 2004/0064091 | A1 | 4/2004 | Keren et al. |
| 2004/0116769 | A1 | 6/2004 | Jassawalla et al. |
| 2004/0167415 | A1 | 8/2004 | Gelfand et al. |
| 2004/0210236 | A1 | 10/2004 | Allers et al. |
| 2004/0260389 | A1 | 12/2004 | Case et al. |
| 2005/0033406 | A1 | 2/2005 | Barnhart et al. |
| 2005/0049692 | A1 | 3/2005 | Numamoto et al. |
| 2005/0079274 | A1 | 4/2005 | Palasis et al. |
| 2006/0106449 | A1 | 5/2006 | Muvhar |
| 2007/0100435 | A1 | 5/2007 | Case et al. |
| 2007/0162103 | A1 | 7/2007 | Case et al. |
| 2007/0208291 | A1 | 9/2007 | Patel |
| 2007/0260327 | A1 | 11/2007 | Case et al. |
| 2008/0103591 | A1 | 5/2008 | Siess |
| 2008/0132748 | A1 | 6/2008 | Shifflette |
| 2008/0154236 | A1 | 6/2008 | Elkins et al. |
| 2008/0183280 | A1 | 7/2008 | Agnew et al. |
| 2009/0024195 | A1 | 1/2009 | Rezai et al. |
| 2009/0062597 | A1 | 3/2009 | Shifflette |
| 2009/0093796 | A1 | 4/2009 | Pfeffer et al. |
| 2009/0264991 | A1 | 10/2009 | Paul, Jr. et al. |
| 2009/0287299 | A1 | 11/2009 | Tabor |
| 2009/0318857 | A1 | 12/2009 | Goodson et al. |
| 2010/0130810 | A1 | 5/2010 | Mohl |
| 2011/0004046 | A1 | 1/2011 | Campbell et al. |
| 2011/0106244 | A1 | 5/2011 | Ferrari et al. |
| 2011/0152999 | A1 | 6/2011 | Hastings et al. |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0257462 | A1 | 10/2011 | Rodefeld et al. |
| 2011/0264075 | A1 | 10/2011 | Leung et al. |
| 2011/0282128 | A1 | 11/2011 | Reitan et al. |
| 2011/0301662 | A1 | 12/2011 | Bar-Yoseph et al. |
| 2012/0022579 | A1 | 1/2012 | Fulton |
| 2012/0059460 | A1 | 3/2012 | Reitan |
| 2012/0089047 | A1 | 4/2012 | Ryba et al. |
| 2012/0116382 | A1 | 5/2012 | Ku et al. |
| 2012/0130469 | A1 | 5/2012 | Cragg et al. |
| 2012/0224970 | A1 | 9/2012 | Schumacher et al. |
| 2012/0237357 | A1 | 9/2012 | Schumacher et al. |
| 2013/0053623 | A1 | 2/2013 | Evans et al. |
| 2013/0053732 | A1 | 2/2013 | Heuser |
| 2013/0177409 | A1 | 7/2013 | Schumacher et al. |
| 2013/0177432 | A1 | 7/2013 | Toellner et al. |
| 2014/0018840 | A1 | 1/2014 | Morgan |
| 2014/0025041 | A1 | 1/2014 | Fukuoka et al. |
| 2014/0128659 | A1 | 5/2014 | Heuring et al. |
| 2014/0275722 | A1 | 9/2014 | Zimmermann et al. |
| 2015/0157777 | A1 | 6/2015 | Tuval |
| 2015/0164662 | A1 | 6/2015 | Tuval |
| 2015/0176582 | A1 | 6/2015 | Liebing |
| 2015/0343136 | A1 | 12/2015 | Nitzan |
| 2015/0343186 | A1 | 12/2015 | Nitzan et al. |
| 2016/0022890 | A1 | 1/2016 | Schwammenthal |
| 2016/0051741 | A1 | 2/2016 | Schwammenthal |
| 2016/0053768 | A1 | 2/2016 | Schumacher et al. |
| 2016/0279310 | A1 | 9/2016 | Scheckel et al. |
| 2017/0100527 | A1 | 4/2017 | Schwammenthal et al. |
| 2018/0303993 | A1 | 10/2018 | Schwammenthal et al. |

FOREIGN PATENT DOCUMENTS

| | | | |
|---|---|---|---|
| WO | 90/13321 | | 11/1990 |
| WO | 1994/01148 | A1 | 1/1994 |
| WO | 99/34847 | | 7/1999 |
| WO | 2001/083016 | | 11/2001 |
| WO | 02/38085 | | 5/2002 |
| WO | 2002/070039 | | 9/2002 |
| WO | 03/006096 | | 1/2003 |
| WO | 03/103745 | | 12/2003 |
| WO | 04/073796 | | 9/2004 |
| WO | 2005/020848 | | 3/2005 |
| WO | 2008/055301 | | 5/2008 |
| WO | 09/010963 | | 1/2009 |
| WO | 2009/129481 | | 10/2009 |
| WO | 2011035926 | A1 | 3/2011 |
| WO | 2011076441 | A1 | 6/2011 |
| WO | 2012007141 | A1 | 1/2012 |
| WO | 13/032849 | | 3/2013 |
| WO | 2013148697 | A1 | 10/2013 |
| WO | 13/183060 | | 12/2013 |
| WO | 2013/183060 | | 12/2013 |
| WO | 14/141284 | | 9/2014 |
| WO | 2015063277 | A2 | 5/2015 |
| WO | 15/177793 | | 11/2015 |
| WO | 16/185473 | | 11/2016 |

OTHER PUBLICATIONS

An Office Action dated Oct. 12, 2017, which issued during the prosecution of U.S. Appl. No. 14/774,081.

U.S. Appl. No. 61/656,244, filed Jun. 6, 2012, Tuval.

International Search Report and Written Opinion from International Application No. PCT/IL2013/050495 dated Nov. 22, 2013.

(56) References Cited

OTHER PUBLICATIONS

International Search Report and Written Opinion for PCT International Application No. PCT/IL2013/050495 dated Sep. 11, 2014.
An International Search Report and a Written Opinion both dated Jan. 27, 2016, which issued during the prosecution of Applicant's PCT/IL2015/050532.
European Search Report dated Jan. 12, 2016, which issued during the prosecution of Applicant's European App No. 13800935.
An Office Action together with the English translation dated Oct. 17, 2016, which issued during the prosecution of Chinese Patent Application No. 201380037335.4.
An Office Action dated Sep. 30, 2016, which issued during the prosecution of Applicant's European Application No. 13800935.
McAlister, et al. "Renal Insufficiency and Heart Failure: Prognostic and Therapeutic Implications From a Prospective Cohort Study", Circulation Journal of the American Heart Association, 2004; 109; pp. 1004-1009.
Forman, et al. "Incidence, Predictors at Admission, and Impact of Worsening Renal Function Among Patients Hospitalized with Heart Failure", Journal of American College of Cardiology, 2004, vol. 43: 61-67.
Hillege et al., "Renal Function as a Predictor of Outcome in a Broad Spectrum of Patients with Heart Failure", Circulation of Journal of the American Heart Association, 2006, vol. 113, pp. 671-678.
Hillege, et al., "Renal Function, Neurohormonal Activation, and Survival in Patients With Chronic Heart Failure", Circulation Journal of the American Heart Association, 2000, vol. 102, pp. 203-210.
Heywood et al., "High Prevalence of Renal Dysfunction and its Impact on Outcome in 118,465 Patients Hospitalized with Acute Decompensated Heart Failure: A Report from the ADHERE Database", Journal of Cardiac Failure, 2007, vol. 13. pp. 422-430.
Yancy, et al., "Clinical Presentation, Management, and In-Hospital Outcomes of Patients Admitted With Acute Decompensated Heart Failure With Preserved Systolic Function. A Report from the Acute Decompensated Heart Failure National Registry (ADHERE) Database", Journal of the American College of Cardiology, 2006, vol. 47(1), pp. 76-84.
Mullens, et al., "Importance of Venous Congestion for Worsening of Renal Function in Advanced Decompensated Heart Failure", Journal of American College of Cardiology, 2009, vol. 53, pp. 589-596.
Damman et al., "Increased Central Venous Pressure is Associated With Impaired Renal Function and Mortality in a Broad Spectrum of Patients With Cardiovascular Disease", Journal of American College of Cardiology, 2009, vol. 53, pp. 582-588.
Uthoff et al., "Central Venous Pressure at Emergency Room Presentation Predicts Cardiac Rehospitalization in Patients With Decompensated Heart Failure", European Journal of Heart Failure, Mar. 11, 2010, vol. 12, 8 pages.
Winton, "The Control of Glomerular Pressure by Vascular Changes Within the Mammalian Kidney, Demonstrated by the Actions of Adrenaline", Journal of Physiology, Nov. 1931, vol. 73: pp. 151-162.
Firth, et al., "Raised Venous Pressure: A Direct Cause of Sodium Retention in Oedema?" The Lancet, May 7, 1988, pp. 1033-1036.
Burnett, et al., "Renal Interstitial Pressure and Sodium Excretion During Renal Vein Constriction", American Physiological Society, 1980, F279-F282.
Doty, et al., "The Effect of Increased Renal Venous Pressure on Renal Function", The Journal of Trauma, vol. 47(6), Dec. 1999, p. 1000-1003.
Felker, et al., "Anemia as a Risk Factor and Therapeutic Target in Heart Failure", Journal of the American College of Cardiology, 2004, vol. 44, pp. 959-966.
Tang, et al., "Anemia in Chronic Heart Failure: Prevalence, Etiology, Clinical Correlates, and Treatment Options", Circulation Journal of the American Heart Association, 2006, vol. 113, pp. 2454-2461.
Mullens, et al., "Elevated Intra-Abdominal Pressure in Acute Decompensated Heart Failure. A Potential Contributor to Worsening Renal Function?", Journal of the American College of Cardiology, 2008, vol. 51, pp. 300-306.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, 2008, vol. 14, pp. 508-514.
Notarius, et al., "Central Venous Pressure During Exercise: Role of Muscle Pump", Canadian Journal of Physiology and Pharmacology, 1996, vol. 74(6), pp. 647-651.
Wood, "The Mechanism of the Increased Venous Pressure With Exercise in Congestive Heart Failure", Journal of Clinical Investigation, 1962, vol. 41(11), pp. 2020-2024.
Lauten, et al., "Heterotopic Transcatheter Tricuspid Valve Implantation: First-In-Man Application of a Novel Approach to Tricuspid Regurgitation", European Heart Journal, Feb. 15, 2011, pp. 1207-1213 (1-7 as printed).
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Gomes et al., "Heterologous Valve Implantation in the Infra-Renal Vena Cava for Treatment of the Iliac Venous Valve Regurgitation Disease: Experimental Study", Rev Bras Cir Cardiovasc, 2002; vol. 17(4): 367-369.
Park et al., "Nutcracker Syndrome: Intravascular Stenting Approach", Nephrol Dial Transplant, 2000, vol. 15, pp. 99-101.
Schmitz-Rode et al., "An Expandable Percutaneous Catheter Pump for Left Ventricular Support", Journal of the American College of Cardiology, 2005, vol. 45, pp. 1856-1861.
Damman et al., "Decreased Cardiac Output, Venous Congestion and the Association With Renal Impairment in Patients With Cardiac Dysfunction", European Journal of Heart Failure, 2007, vol. 9, pp. 872-878.
Winton, "The Influence of Venous Pressure on the Isolated Mammalian Kidney", Journal of Physiology, Jun. 6, 1931, vol. 72(1), pp. 49-61.
Wencker, "Acute Cardio-Renal Syndrome: Progression From Congestive Heart Failure to Congestive Kidney Failure", Current Heart Failure Reports, 2007, vol. 4, pp. 134-138.
Semple et al., "Effect OfIncreased Renal Venous Pressure on Circulatory "Autoregulation" Of Isolated Dog Kidneys", Circulation Research Journal of The American Heart Association, 1959, vol. 7, pp. 643-648.
Raddy et al., "Effect of Elevation of Intraluminal Pressure on Renal Vascular Resistance", Circulation Research Journal of The American Heart Association, 1956, Vole. 4, pp. 659-663.
Ikari, "The Physics of Guiding Catheter; The IKARI Guiding Catheter in TRI", available at httu:i/www.docstoc.com/docs/148136553/The-[KARI-catheter---anovel-guide-for-TRI--, uploaded on Mar. 8, 2013.
U.S. Appl. No. 14/405,144, dated Feb. 22, 2016, Office Action.
U.S. Appl. No. 14/405,144, dated Jul. 14, 2016, Office Action.
Japanese Office Action for Japanese Patent Application No. 2015-562562 dated Jun. 13, 2018.
Non-Final Office Action for U.S. Appl. No. 16/022,445 dated Aug. 9, 2018.
European Search Report for European Application No. 14762232.8 dated Sep. 28, 2016.
Final Office Action for U.S. Appl. No. 14/931,363 dated Jun. 1, 2017.
Final Office Action for US. Appl. No. 15/312,034 dated Jan. 17, 2019.
International Search Report and Written Opinion for International Application No. PCT/IL2016/050525 dated Oct. 14, 2016.
Invitation to pay additional fees for International Application No. PCT/IL2015/050532 dated Nov. 17, 2015.
Issue Notification for U.S. Appl. No. 14/931,363 dated Feb. 21, 2018.
Japanese Office Action for Japanese Patent Application No. 2015562562 dated on Oct. 27, 2017.

(56) References Cited

OTHER PUBLICATIONS

Non-Final Office Action for U.S. Appl. No. 14/567,439 dated Nov. 16, 2016.
Non-Final Office Action for U.S. Appl. No. 14/774,081 dated May 24, 2017.
Non-Final Office Action for U.S. Appl. No. 14/931,363 dated Feb. 15, 2017.
Non-Final Office Action for U.S. Appl. No. 14/931,363 dated Oct. 3, 2016.
Notice of Allowance for U.S. Appl. No. 14/567,439 dated Jun. 2, 2017.
Notice of Allowance for U.S. Appl. No. 14/774,081 dated Apr. 11, 2018.
Notice of Allowance for U.S. Appl. No. 14/931,363 dated Dec. 12, 2017.
Notice of Allowance for U.S. Appl. No. 14/931,363 dated Oct. 12, 2017.
Office Action for Chinese Patent Application No. 201380037335.4 dated Mar. 22, 2017.
Restriction Requirement for U.S. Appl. No. 14/567,439 dated Aug. 23, 2016.
Restriction Requirement for U.S. Appl. No. 14/774,081 dated Mar. 9, 2017.
Restriction Requirement for U.S. Appl. No. 14/931,363 dated Jul. 22, 2016.
U.S. Appl. No. 61/656,244 filed Jun. 6, 2013.
U.S. Appl. No. 61/779,803 filed Mar. 13, 2013.
U.S. Appl. No. 61/914,470 filed Dec. 11, 2013.
U.S. Appl. No. 61/914,475 filed Dec. 11, 2013.
U.S. Appl. No. 62/000,192 filed May 19, 2014.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart.", Expert review of cardiovascular therapy, 7.9, 2009, pp. 1067-1077.
Fraser, et al., "The use of computational fluid dynamics in the development of ventricular assist devices.", Medical engineering & physics, 33.3, 2011, pp. 263-280.
Hsu, et al., "Review of recent patents on foldable ventricular assist devices.", Recent Patents on Biomedical Engineering, 5.3, 2012, pp. 208-222.
Kafagy, et al., "Design of axial blood pumps for patients with dysfunctional fontan physiology: computational studies and performance testing.", Artificial organs, 39.1, 2015, pp. 34-42.
Kang, et al., "Fluid dynamics aspects of miniaturized axial-flow blood pump.", Bio-medical materials and engineering, 24.1, 2014, pp. 723-729.
Koochaki, et al., "A new design and computational fluid dynamics study of an implantable axial blood pump.", Australasian Physical & Engineering Sciences in Medicine, 36.4, 2013, pp. 417-422.
Reul, et al., "Blood pumps for circulatory support.", Perfusion-Sevenoaks, 15.4, 2000, pp. 295-312.
Song, et al., "Axial flow blood pumps.", ASAIO journal, 49, 2003, pp. 355-364.
Throckmorton, et al., "Design of a protective cage for an intra vascular axial flow blood pump to mechanically assist the failing Fontan.", Artificial organs, 33.8, 2009, pp. 611-621.
Thunberg, et al., "Ventricular assist devices today and tomorrow.", Journal of cardiothoracic and vascular anesthesia, 24.4, 2010, pp. 656-680.
Timms, "A review of clinical ventricular assist devices.", Medical engineering & Physics, 33.9, 2011, pp. 1041-1047.
Wu, et al., "Design and simulation of axial flow maglev blood pump.", International Journal of Information Engineering and Electronics Business, 3.2, 2011, p. 42.
Notice of Allowance for U.S. Appl. No. 15/423,368 dated Nov. 13, 2018.
Notice of Allowance for U.S. Appl. No. 16/022,445 dated Mar. 18, 2019.
U.S. Appl. No. 14/405,144 filed Dec. 2, 2014.
U.S. Appl. No. 14/774,081 filed Sep. 9, 2015.
U.S. Appl. No. 15/423,368 filed Feb. 2, 2017.
U.S. Appl. No. 16/022,445 filed Jun. 28, 2018.
U.S. Appl. No. 16/273,898 filed Feb. 12, 2019.
U.S. Appl. No. 16/278,323 filed Feb. 18, 2019.
U.S. Appl. No. 16/281,385 filed Feb. 21, 2019.

VENA-CAVAL DEVICE

CROSS-REFERENCES TO RELATED APPLICATIONS

The present application is a continuation of U.S. patent application Ser. No. 14/405,144 filed on Dec. 2, 2014 (published as US 2015/0164662), which is the US national phase application of PCT Application No. PCT/IL2013/050495 filed on Jun. 6, 2013 (published as WO 2013/183060), which claims priority to U.S. Provisional Patent Application No. 61/656,244 filed on Jun. 6, 2012. Each of the foregoing applications is incorporated herein, in its entirety, by this reference.

FIELD OF EMBODIMENTS OF THE INVENTION

Some applications of the present invention generally relate to medical apparatus. Specifically, some applications of the present invention relate to apparatus and methods associated with placing a valve in one or more of a subject's renal veins.

BACKGROUND

It is common for cardiac dysfunction or congestive heart failure to develop into kidney dysfunction, which in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: a reduction in the kidney's erythropoietin production, hemodilution by fluid retention, and an inflammatory response leading to a reduced gastro-intestinal iron uptake.

Mechanistically, increased renal venous pressure, may cause intracapsular pressure and, subsequently, interstitial peritubular pressure, to rise. A rise in peritubular pressure may impact tubular function (reduce sodium excretion), as well as diminish glomerular filtration by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration) has been shown to reduce plasma creatinine levels.

Increased venous return resulting from activation of the "leg muscle pump" during physical activity such as walking may raise systemic venous pressure, particularly in heart failure patients, and may result in reflux into the renal veins.

SUMMARY OF EMBODIMENTS

For some applications of the present invention, a device is placed in at least one of a subject's renal veins, the device being configured to reduce pressure at the subject's kidney relative to the subject's central venous pressure. The device is typically a passive device, i.e., the device is configured to reduce pressure at the subject's kidney without requiring external energy to be supplied to the device (e.g., from a power supply or a battery). When the device is in a deployed state inside the renal vein, any movement of any portion of the device is caused by blood flow and/or pressure that is imparted to the portion of the device rather than being caused by energy that is imparted to the device (e.g., from a power supply and/or a battery).

Typically, the device reduces pressure at the subject's kidney by reducing the back flow of blood toward the kidney via the renal vein, and/or by reducing renal venous pressure relative to central venous pressure, by protecting the renal vein from high central venous pressures. Further typically, the device is placed inside the renal vein in response to identifying the subject as suffering from a condition that causes the subject to have elevated central venous pressure relative to that of a healthy subject. For some applications, the condition includes cardiac dysfunction, congestive heart failure, low renal blood flow, high renal vascular resistance, arterial hypertension, kidney dysfunction, and/or cardio-renal syndrome. For some applications, at least one of the devices is placed in each of the subject's left and right renal veins.

For some applications, the device is placed in the renal vein temporarily in order to provide an acute treatment for one or more of the above-listed conditions. For example, the valve may be placed in a renal vein for a period of more than 12 hours (e.g., more than 24 hours), and/or less than three months (e.g., less than one month), during which the subject is undergoing an acute episode of heart failure, and subsequently, the valve may be retrieved from the renal vein.

Typically a prosthetic valve is placed (e.g., transcatheterally placed) inside the renal vein. The valve reduces pressure at the subject's kidney by reducing the back flow of blood toward the kidney via the renal vein, by the valve closing in response to blood flowing back into the renal vein. Alternatively or additionally, the valve protects the renal vein from pressure increases resulting from high central venous pressures, by the valve closing in response to pressure within the vena cava being greater than a threshold pressure.

Typically, placement of the device inside the renal vein causes an improvement of renal function and/or prevention or a reduction in deterioration of the subject's renal function. The device typically reduces renal venous and interstitial pressure, thereby causing a decrease in parenchymal ischemia and injury, and/or an increase in renal blood flow, glomerular filtration rate, and/or in erythropoetin production. For some applications, the device improves the subject's cardiac function, e.g., by reducing afterload. For some applications, the device improves the subject's cardiac and/ or renal function, e.g., by causing improved renal salt and water excretion, by suppressing renin-angiotensin-aldosterone system (RAAS) activation, by suppressing arginine-vasopressin system activation, and/or by suppressing the sympathetic nervous system.

For some applications, placement of the device inside the renal vein causes renal venous pressure to decrease such as to prevent or diminish a rise in renal parenchymal intracapsular pressure as a result of increased pressure and backflow from the inferior vena cava to the renal vein (e.g., backflow from the heart and/or from the veins of the lower body towards the renal vein). For some applications, placement of the device inside the renal vein reduces deterioration, or promotes recovery of renal function in a patient with acute or chronic heart failure. For some applications, placement of the device inside the renal vein blocks or attenuates the activation of neural and endocrine control axes which generate the physiological effects that are responsible for the development and sustainment of the heart failure syndrome.

There is therefore provided, in accordance with some applications of the present invention, apparatus including:

a valve including:

valve leaflets; and a non-branched valve frame configured to support the valve leaflets, the frame defining a single longitudinal axis thereof, the longitudinal axis being a generally straight line along a full length of the frame;

the valve being configured:

to be placed at least partially within a renal vein of a subject, to define an open state thereof in which the valve leaflets allow generally unimpeded antegrade blood flow therethrough, and to define a closed state thereof in which the valve leaflets, in a passive manner, reduce venous pressure within the renal vein relative to central venous pressure of the subject.

For some applications, the valve is configured to be placed entirely within the subject's renal vein.

For some applications, the valve is configured in the closed state thereof to reduce venous pressure within the renal vein relative to central venous pressure of the subject even in an absence of any device being placed at a location that is within an abdomen of the subject and outside a venous system of the subject.

For some applications, the valve frame is configured to reduce compression of the renal vein resulting from intra-abdominal pressure that is exerted on the renal vein, relative to a level of compression of the renal vein resulting from intra-abdominal pressure that is exerted on the renal vein in an absence of the valve frame.

For some applications, the valve frame defines:

a narrow portion thereof to which the valve leaflets are coupled, and a bulging portion that is bulged with respect to the narrow portion, and that is configured to cause the renal vein to form a bulged portion in a vicinity of the valve leaflets.

For some applications, the valve is configured to be placed in the renal vein for a period of less than three months, and subsequently, to be retrieved from the subject's renal vein.

For some applications, the valve is configured to be placed in the renal vein for a period of less than one month, and subsequently, to be retrieved from the subject's renal vein.

For some applications, the valve frame defines:

a cylindrical portion thereof that defines an outer surface thereof, the valve leaflets being coupled to the cylindrical portion, and at least one protruding portion thereof, the protruding portion being shaped such as to diverge radially from the outer surface of the cylindrical portion, such that a separation between the protruding portion and the outer surface of the cylindrical portion is greater at a downstream end of the protruding portion than at an upstream end of the protruding portion.

For some applications, the protruding portion is shaped to be disposed outside of radial projections of downstream edges of the valve leaflets, such that even when the valve leaflets are in open states thereof, the valve leaflets do not contact the protruding portion.

For some applications, the valve leaflets are coupled to the frame downstream of the protruding portion, such that an upstream end of each of the valve leaflets is longitudinally spaced from a downstream end of the protruding portion.

For some applications, the cylindrical portion and the protruding portion are reversibly couplable to one another.

For some applications, the protruding portion diverges from the outer surface of the cylindrical portion at an angle of greater than 40 degrees with respect to the outer surface of downstream portion of the cylindrical portion.

For some applications, the protruding portion diverges from the outer surface of the cylindrical portion at an angle of greater than 50 degrees with respect to the outer surface of downstream portion of the cylindrical portion.

There is further provided, in accordance with some applications of the present invention, a method including:

identifying a subject as suffering from a condition that causes the subject to have elevated central venous pressure; and in response thereto, reducing blood pressure within a renal vein of the subject relative to the subject's central venous pressure, by placing a device at least partially within the subject's renal vein, the device being configured, in a passive manner, to reduce venous pressure within the subject's renal vein relative to central venous pressure of the subject.

For some applications, placing the device at least partially within the renal vein includes placing the device entirely within the renal vein.

For some applications, reducing pressure within the renal vein includes reducing pressure within the renal vein by placing the device at least partially within the renal vein in an absence of any device being placed at a location that is within an abdomen of the subject and outside a venous system of the subject.

For some applications, identifying the subject as suffering from the condition that causes the subject to have elevated central venous pressure includes identifying the subject as suffering from elevated renal venous pressure that is substantially due to the subject suffering from elevated central venous pressure.

For some applications, identifying the subject as suffering from the condition that causes the subject to have elevated central venous pressure includes identifying the subject as suffering from elevated renal venous pressure even in an absence of a condition that causes renal venous pressure of the subject to be elevated due to pressure being exerted on the subject's renal vein through walls of the subject's renal vein from a location outside the renal vein.

For some applications, identifying the subject as suffering from the condition that causes the subject to have elevated central venous pressure includes identifying the subject as suffering from elevated central venous pressure even in an absence of the subject suffering from tricuspid valve regurgitation.

For some applications, placing the device in the subject's renal vein includes placing a first device in a left renal vein of the subject and placing a second device in a right renal vein of the subject.

For some applications, reducing the blood pressure within the renal vein includes treating anemia of the subject that is related to the subject's condition, by reducing the blood pressure within the renal vein.

For some applications, reducing the blood pressure within the renal vein includes reducing the blood pressure within the subject's renal vein relative to central venous pressure of the subject, even during lower body exercise that is performed by the subject.

For some applications, identifying the subject as suffering from the condition includes identifying the subject as suffering from a condition selected from the group consisting of: cardiac dysfunction, congestive heart failure, and kidney dysfunction.

For some applications, identifying the subject as suffering from the condition includes identifying the subject as suffering from a condition selected from the group consisting of: cardiac dysfunction, and congestive heart failure.

For some applications, placing the device at least partially within the subject's renal vein includes placing the device at least partially within the subject's renal vein for a period of less than three months, and subsequently, retrieving the device from the subject's renal vein.

For some applications, placing the device at least partially within the subject's renal vein includes placing the device at least partially within the subject's renal vein for a period of less than one month, and subsequently, retrieving the device from the subject's renal vein.

For some applications, reducing the blood pressure within the renal vein includes treating the subject's condition, by reducing the blood pressure within the renal vein.

For some applications, treating the subject's condition includes reducing activation of a neurohormonal pathway of the subject, by reducing the blood pressure within the renal vein.

For some applications, placing the device in the subject's renal vein includes placing a valve in the subject's renal vein.

For some applications, placing the valve at least partially within the subject's renal vein, includes placing at least partially within the subject's renal vein a valve that includes valve leaflets, such that in an open state of the valve, the valve leaflets allow generally unimpeded antegrade blood flow therethrough.

For some applications, placing the valve in the subject's renal vein includes reducing compression of the renal vein resulting from intra-abdominal pressure that is exerted on the renal vein, relative to a level of compression of the renal vein resulting from intra-abdominal pressure that is exerted on the renal vein in an absence of the valve.

For some applications, placing the valve at least partially within the renal vein includes forming a bulged portion within the subject's renal vein by placing at least partially within the renal vein a valve that includes:

a narrow portion thereof to which the valve leaflets are coupled, and a bulging portion that is bulged with respect to the narrow portion, and that is configured to cause the renal vein to form a bulged portion in a vicinity of the valve leaflets.

For some applications, placing the valve at least partially within the renal vein includes forming a bulged portion within the subject's renal vein by placing at least partially within the renal vein a valve that includes:

valve leaflets; and a frame configured to support the valve leaflets, the frame defining:

- a cylindrical portion thereof that defines an outer surface thereof, and
- at least one protruding portion thereof, the protruding portion being shaped such as to form the bulged portion by diverging radially from the outer surface of the cylindrical portion, such that a separation between the protruding portion and the outer surface of the cylindrical portion is greater at a downstream end of the protruding portion than at an upstream end of the protruding portion.

For some applications, placing the valve at least partially within the renal vein includes placing at least partially within the renal vein a valve, the protruding portion of the valve being shaped to be disposed outside of radial projections of downstream edges of the valve leaflets, such that even when the valve leaflets are in open states thereof, the valve leaflets do not contact the protruding portion.

For some applications, placing the valve at least partially within the renal vein includes placing the valve at least partially within the renal vein, the valve leaflets of the valve being coupled to the frame downstream of the protruding portion, such that an upstream end of each of the valve leaflets is longitudinally spaced from a downstream end of the protruding portion.

For some applications, the valve includes a valve, the cylindrical portion and the protruding portion of which are couplable to one another, and placing the valve at least partially within the renal vein includes:

placing the protruding portion at least partially within the renal vein, and subsequently, placing the cylindrical portion at least partially within the renal vein and coupling the cylindrical portion to the protruding portion.

For some applications, the valve includes a valve, the cylindrical portion and the protruding portion of which are reversibly couplable to one another, and the method further includes:

subsequent to placing the valve at least partially within the renal vein,

- decoupling the cylindrical portion from the protruding portion; and
- removing the cylindrical portion from the renal vein, while leaving the protruding portion at least partially within the renal vein.

For some applications, placing the valve at least partially within the renal vein includes placing at least partially within the renal vein a valve, the protruding portion of the valve diverging from the outer surface of the cylindrical portion of the valve at an angle of greater than 40 degrees with respect to the outer surface of downstream portion of the cylindrical portion.

For some applications, placing the valve at least partially within the renal vein includes placing at least partially within the renal vein a valve, the protruding portion of the valve diverging from the outer surface of the cylindrical portion of the valve at an angle of greater than 50 degrees with respect to the outer surface of downstream portion of the cylindrical portion.

For some applications, placing the valve at least partially within the renal vein includes placing the valve at least partially within the renal vein such that the valve leaflets are disposed within the bulged portion.

For some applications, placing the valve at least partially within the renal vein such that the valve leaflets are disposed within the bulged portion includes generating fluid flow dynamics in a vicinity of the leaflets that are such as to reduce stagnation of blood in the vicinity of the leaflets.

For some applications, placing the valve at least partially within the renal vein such that the valve leaflets are disposed within the bulged portion includes generating fluid flow dynamics in a vicinity of the leaflets that are such as to cause the leaflets to open in response to antegrade blood flow in the vicinity of the leaflets.

For some applications, placing the valve at least partially within the renal vein such that the valve leaflets are disposed within the bulged portion includes placing bases of the leaflets in a vicinity of a region of the bulged portion at which a cross sectional area of the bulged portion is at a maximum value thereof.

For some applications, placing the valve at least partially within the renal vein such that the valve leaflets are disposed within the bulged portion includes generating fluid flow dynamics in a vicinity of the leaflets that are such as to cause the leaflets to close in response to antegrade blood flow in the vicinity of the leaflets.

For some applications, placing the valve at least partially within the renal vein such that the valve leaflets are disposed within the bulged portion includes placing bases of the leaflets in a widening region of the bulged portion.

For some applications, placing the valve at least partially within the renal vein includes deforming at least a portion of a junction between the renal vein and a vena cava of the subject, by placing the valve at least partially within the renal vein such that a portion of the valve is disposed in a vicinity of the junction, the portion of the valve being shaped such as to deform the portion of the junction.

For some applications, the valve includes valve leaflets, and placing the valve at least partially within the renal vein includes placing the valve at least partially within the renal vein such that the valve leaflets are disposed within the cavity at the portion of the junction.

For some applications, placing the valve at least partially within the renal vein such that the valve leaflets are disposed within the cavity at the portion of the junction includes generating fluid flow dynamics in a vicinity of the leaflets that are such as to cause the leaflets to open in response to antegrade blood flow in the vicinity of the leaflets.

For some applications, placing the valve at least partially within the renal vein such that the valve leaflets are disposed within the cavity at the portion of the junction includes generating fluid flow dynamics in a vicinity of the leaflets that are such as to reduce stagnation of blood in the vicinity of the leaflets.

For some applications, placing the valve at least partially within the renal vein such that the valve leaflets are disposed within the cavity at the portion of the junction includes generating fluid flow dynamics in a vicinity of the leaflets that are such as to cause the leaflets to close in response to antegrade blood flow in the vicinity of the leaflets.

For some applications, the valve includes:

valve leaflets; and a frame configured to support the valve leaflets, the frame defining:

a cylindrical portion thereof that defines an outer surface thereof, the valve leaflets being coupled to a downstream portion of the cylindrical portion, and at least one protruding portion thereof, the protruding portion being shaped such as to protrude radially from the outer surface of the cylindrical portion, and deforming at least the portion of the junction includes deforming the portion of the junction with the at least one protruding portion.

For some applications, the valve includes a valve, the at least one protruding portion of which diverges radially from the outer surface of the cylindrical portion, such that a separation between the protruding portion and the outer surface of the cylindrical portion is greater at a downstream end of the protruding portion than at an upstream end of the protruding portion, and deforming at least the portion of the junction includes deforming the portion of the junction with the at least one protruding portion.

For some applications, the valve includes a valve, the cylindrical portion and the protruding portion of which are couplable to one another, and placing the valve at least partially within the renal vein includes:

placing the protruding portion at least partially within the renal vein, and subsequently, placing the cylindrical portion at least partially within the renal vein and coupling the cylindrical portion to the protruding portion.

For some applications, the valve includes a valve, the cylindrical portion and the protruding portion of which are reversibly couplable to one another, and the method further includes:

subsequent to placing the valve at least partially within the renal vein, decoupling the cylindrical portion from the protruding portion; and removing the cylindrical portion from the renal vein, while leaving the protruding portion at least partially within the renal vein.

There is further provided, in accordance with some applications of the present invention, a method including:

identifying a junction between a first vein, and a second vein, the first vein being a tributary of the second vein; and deforming at least a portion of the junction such that the portion of the junction defines a cavity, by placing a valve within the first vein, in a vicinity of the junction, a portion of the valve being shaped such as to deform the portion of the junction.

For some applications, the valve includes:

valve leaflets; and a frame configured to support the valve leaflets, the frame defining:

a narrow portion thereof to which the valve leaflets are coupled, and a bulging portion that is bulged with respect to the narrow portion, and deforming at least the portion of the junction includes deforming the portion of the junction with the bulging portion.

For some applications, the valve includes valve leaflets, and placing the valve within the first vein includes placing the valve within the first vein such that the valve leaflets are disposed within the cavity at the portion of the junction.

For some applications, placing the valve within the first vein such that the valve leaflets are disposed within the cavity at the portion of the junction includes generating fluid flow dynamics in a vicinity of the leaflets that are such as to cause the leaflets to open in response to antegrade blood flow in the vicinity of the leaflets.

For some applications, placing the valve within the first vein such that the valve leaflets are disposed within the cavity at the portion of the junction includes generating fluid flow dynamics in a vicinity of the leaflets that are such as to reduce stagnation of blood in the vicinity of the leaflets.

For some applications, placing the valve within the first vein such that the valve leaflets are disposed within the cavity at the portion of the junction includes generating fluid flow dynamics in a vicinity of the leaflets that are such as to cause the leaflets to close in response to antegrade blood flow in the vicinity of the leaflets.

For some applications, the valve includes:

valve leaflets; and a frame configured to support the valve leaflets, the frame defining:

a cylindrical portion thereof that defines an outer surface thereof, the valve leaflets being coupled to a downstream portion of the cylindrical portion, and at least one protruding portion thereof, the protruding portion being shaped such as to protrude radially from the outer surface of the cylindrical portion, and deforming at least the portion of the junction includes deforming the portion of the junction with the at least one protruding portion.

For some applications, the valve includes a valve, the at least one protruding portion of which diverges radially from the outer surface of the cylindrical portion, such that a separation between the protruding portion and the outer surface of the cylindrical portion is greater at a downstream end of the protruding portion than at an upstream end of the protruding portion, and deforming at least the portion of the junction includes deforming the portion of the junction with the at least one protruding portion.

For some applications, the valve includes a valve, the cylindrical portion and the protruding portion of which are couplable to one another, and placing the valve within the first vein includes:

placing the protruding portion within the first vein, and subsequently, placing the cylindrical portion within the first vein and coupling the cylindrical portion to the protruding portion.

For some applications, the valve includes a valve, the cylindrical portion and the protruding portion of which are reversibly couplable to one another, and the method further includes:

subsequent to placing the valve within the first vein, decoupling the cylindrical portion from the protruding portion; and removing the cylindrical portion from the first vein, while leaving the protruding portion within the first vein.

There is further provided, in accordance with some applications of the present invention, apparatus for use with a blood vessel, including:

a valve including:

valve leaflets; and a frame configured to support the valve leaflets, the frame defining:

a cylindrical portion thereof that defines an outer surface thereof, and at least one protruding portion thereof, the protruding portion being shaped such as to diverge radially from the outer surface of the cylindrical portion, such that a separation between the protruding portion and the outer surface of the cylindrical portion is greater at a downstream end of the protruding portion than at an upstream end of the protruding portion, the valve leaflets being coupled to the frame downstream of the protruding portion, such that an upstream end of each of the valve leaflets is longitudinally spaced from a downstream end of the protruding portion.

For some applications, the cylindrical portion and the protruding portion are reversibly couplable to one another.

There is further provided, in accordance with some applications of the present invention, apparatus for use with a blood vessel, including:

a valve including:

valve leaflets; and a frame configured to support the valve leaflets, the frame defining:

a cylindrical portion thereof that defines an outer surface thereof, the valve leaflets being coupled to a downstream portion of the cylindrical portion, and at least one protruding portion thereof, the protruding portion being shaped such as to diverge radially from the outer surface of the cylindrical portion, such that a separation between the protruding portion and the outer surface of the cylindrical portion is greater at a downstream end of the protruding portion than at an upstream end of the protruding portion, the protruding portion diverging from the outer surface of the cylindrical portion at an angle of greater than 40 degrees with respect to the outer surface of downstream portion of the cylindrical portion.

For some applications, the cylindrical portion and the protruding portion are reversibly couplable to one another.

For some applications, the protruding portion diverges from the outer surface of the cylindrical portion at an angle of greater than 50 degrees with respect to the outer surface of downstream portion of the cylindrical portion.

There is further provided, in accordance with some applications of the present invention, a method including:

forming a bulged portion within a vein of a subject, by placing within the vein a valve that includes:

valve leaflets; and a frame configured to support the valve leaflets, the frame defining:

a cylindrical portion thereof that defines an outer surface thereof, and at least one protruding portion thereof, the protruding portion being shaped such as to form the bulged portion by diverging radially from the outer surface of the cylindrical portion, such that a separation between the protruding portion and the outer surface of the cylindrical portion is greater at a downstream end of the protruding portion than at an upstream end of the protruding portion, the valve leaflets being coupled to the frame downstream of the protruding portion, such that an upstream end of each of the valve leaflets is longitudinally spaced from a downstream end of the protruding portion.

For some applications, the valve includes a valve, the cylindrical portion and the protruding portion of which are couplable to one another, and placing the valve within the vein includes:

placing the protruding portion within the first vein, and subsequently, placing the cylindrical portion within the vein and coupling the cylindrical portion to the protruding portion.

For some applications, the valve includes a valve, the cylindrical portion and the protruding portion of which are reversibly couplable to one another, and the method further includes:

subsequent to placing the valve within the vein, decoupling the cylindrical portion from the protruding portion; and removing the cylindrical portion from the vein, while leaving the protruding portion within the vein.

For some applications, placing the valve within the vein includes placing the valve within the vein such that the valve leaflets are disposed within the bulged portion.

For some applications, placing the valve within the vein such that the valve leaflets are disposed within the bulged portion includes generating fluid flow dynamics in a vicinity of the leaflets that are such as to reduce stagnation of blood in the vicinity of the leaflets.

For some applications, placing the valve within the vein such that the valve leaflets are disposed within the bulged portion includes generating fluid flow dynamics in a vicinity of the leaflets that are such as to cause the leaflets to open in response to antegrade blood flow in the vicinity of the leaflets.

For some applications, placing the valve within the vein such that the valve leaflets are disposed within the bulged portion includes placing bases of the leaflets in a vicinity of a region of the bulged portion at which a cross sectional area of the bulged portion is at a maximum value thereof.

For some applications, placing the valve within the vein such that the valve leaflets are disposed within the bulged portion includes generating fluid flow dynamics in a vicinity of the leaflets that are such as to cause the leaflets to close in response to antegrade blood flow in the vicinity of the leaflets.

For some applications, placing the valve within the vein such that the valve leaflets are disposed within the bulged portion includes placing bases of the leaflets in a widening region of the bulged portion.

There is further provided, in accordance with some applications of the present invention, a method including:

identifying a subject as suffering from a condition selected from the group consisting of: cardiac dysfunction, congestive heart failure, and kidney dysfunction; and in response thereto, placing a stent at least partially within a renal vein of the subject, such as to reduce pressure within the renal vein relative to the pressure within the renal vein in the absence of the stent.

For some applications, identifying the subject as suffering from the condition includes identifying the subject as suffering from a condition selected from the group consisting of: cardiac dysfunction, and congestive heart failure.

There is further provided, in accordance with some applications of the present invention, apparatus for use with a blood vessel, including:

a valve including:

valve leaflets; and a frame configured to support the valve leaflets, the frame defining:

a cylindrical portion thereof that defines an outer surface thereof, the valve leaflets being coupled to a downstream portion of the cylindrical portion, and at least one protruding portion thereof, the protruding portion being shaped such as to diverge radially from the outer surface of the cylindrical portion, such that a separation between the protruding portion and the outer surface of the cylindrical portion is greater at a downstream end of the protruding portion than at an upstream end of the protruding portion, the protruding portion being shaped to be disposed outside of radial projections of downstream edges of the valve leaflets, such that even when the valve leaflets are in open states thereof, the valve leaflets do not contact the protruding portion.

There is further provided, in accordance with some applications of the present invention, a method for use with renal veins and a vena cava of a subject, the method including:

identifying the subject as suffering from a condition that causes the subject to have elevated central venous pressure; and in response thereto, reducing blood pressure within the subject's renal veins relative to the subject's central venous pressure, by directing antegrade blood flow through the subject's vena cava past the subject's renal veins, by placing a nozzle inside the subject's vena cava.

For some applications, placing the nozzle inside the vena cava includes placing the nozzle inside the vena cava at a location that is upstream of junctions of the vena cava with the subject's renal veins, the method further including placing a valve inside the subject's vena cava at a location that is downstream of the junctions of the vena cava with the subject's renal veins.

There is further provided, in accordance with some applications of the present invention, apparatus for use with renal veins and a vena cava of a subject, the apparatus including:

a valve including:

a valve frame configured to be placed at least partially inside the vena cava; and valve leaflets that are coupled to the valve frame such that when the valve frame is placed at least partially inside the vena cava, the valve leaflets are disposed in vicinities of ostia of junctions between the vena cava and the renal veins, such that the valve leaflets are configured to:

open in response to antegrade blood flow from the renal veins into the vena cava, and close in response to retrograde blood flow from the vena cava into the renal veins.

For some applications, the valve frame includes a central portion that is configured to be placed inside the vena cava and side branches that branch from the central portion and that are configured to be placed at least partially inside respective renal veins, and the valve leaflets are coupled to the side branches.

For some applications, the valve leaflets are coupled to the valve frame such that when the valve frame is placed at least partially inside the vena cava, the valve leaflets are disposed inside the vena cava in the vicinities of the ostia of the junctions between the vena cava and the renal veins.

For some applications, the valve leaflets are coupled to the valve frame such that when the valve frame is placed at least partially inside the vena cava, the valve leaflets are disposed inside the renal veins in the vicinities of the ostia of the junctions between the vena cava and the renal veins.

There is further provided, in accordance with some applications of the present invention, a method for use with renal veins and a vena cava of a subject, the method including:

identifying a subject as suffering from a condition that causes the subject to have elevated central venous pressure; and in response thereto, reducing blood pressure within the subject's renal veins relative to the subject's central venous pressure, by placing a valve frame at least partially inside the subject's vena cava, such that valve leaflets that are coupled to the valve frame are disposed in vicinities of ostia of junctions between the vena cava and the renal veins, and such that the valve leaflets are configured to:

open in response to antegrade blood flow from the renal vein into the vena cava, and close in response to retrograde blood flow from the vena cava into the renal vein.

For some applications, the valve frame includes a central portion and side branches that branch from the central portion, the valve leaflets being coupled to the side branches, and placing the valve frame at least partially inside the subject's vena cava includes placing the central portion of the valve frame inside the vena cava and placing the side branches of the valve frame at least partially inside respective renal veins.

For some applications, placing the valve frame at least partially inside the subject's vena cava includes placing the valve frame at least partially inside the subject's vena cava such that the valve leaflets are disposed inside the vena cava in the vicinities of the ostia of the junctions between the vena cava and the renal veins.

For some applications, placing the valve frame at least partially inside the subject's vena cava includes placing the valve frame at least partially inside the subject's vena cava such that the valve leaflets are disposed inside the renal veins in the vicinities of the ostia of the junctions between the vena cava and the renal veins.

The present invention will be more fully understood from the following detailed description of embodiments thereof, taken together with the drawings, in which:

DETAILED DESCRIPTION OF EMBODIMENTS

Figure 1A:
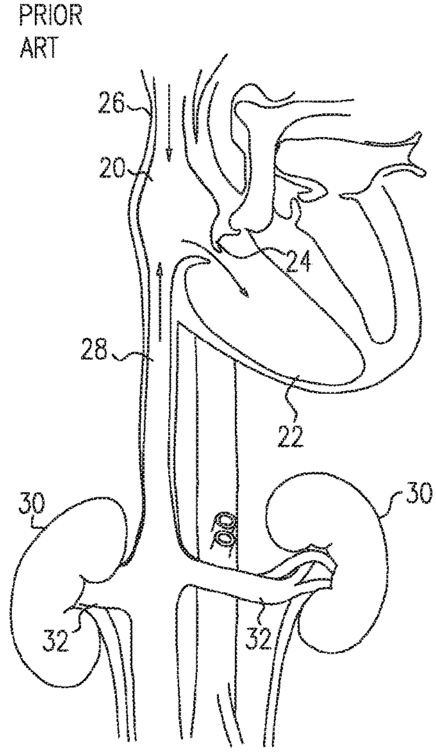
FIGS. 1A-B are schematic illustrations of a healthy subject's right heart during diastole and systole respectively.
Figure 1B:
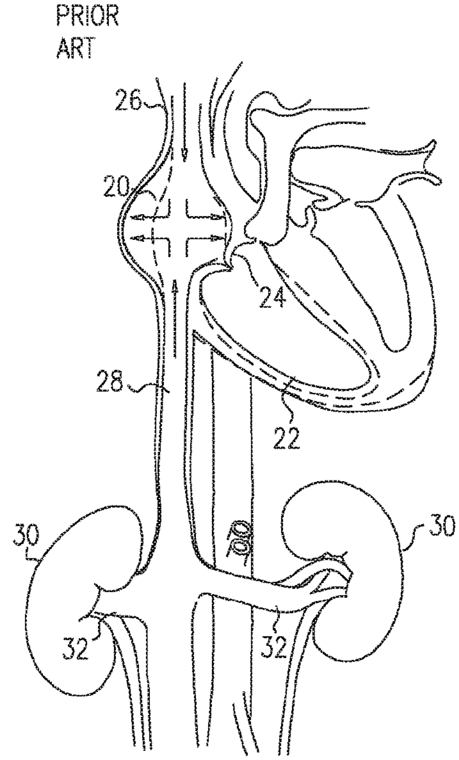

Reference is now made to FIGS. 1A-B, which are schematic illustrations of a healthy subject's heart during diastole and systole respectively. As shown in FIG. 1A, during diastole, blood flows from the subject's right atrium 20 to the subject's right ventricle 22. As shown in FIG. 1B, during ventricular systole, the tricuspid valve 24, which separates the right ventricle from the right atrium, closes, as the right ventricle pumps blood toward the subject's lungs. During systolic long-axis contraction of the right ventricle, the right atrium fills with blood from the superior vena cava 26 and the inferior vena cava 28, the right atrium expanding such as to draw blood into the right atrium.

Figure 1C:
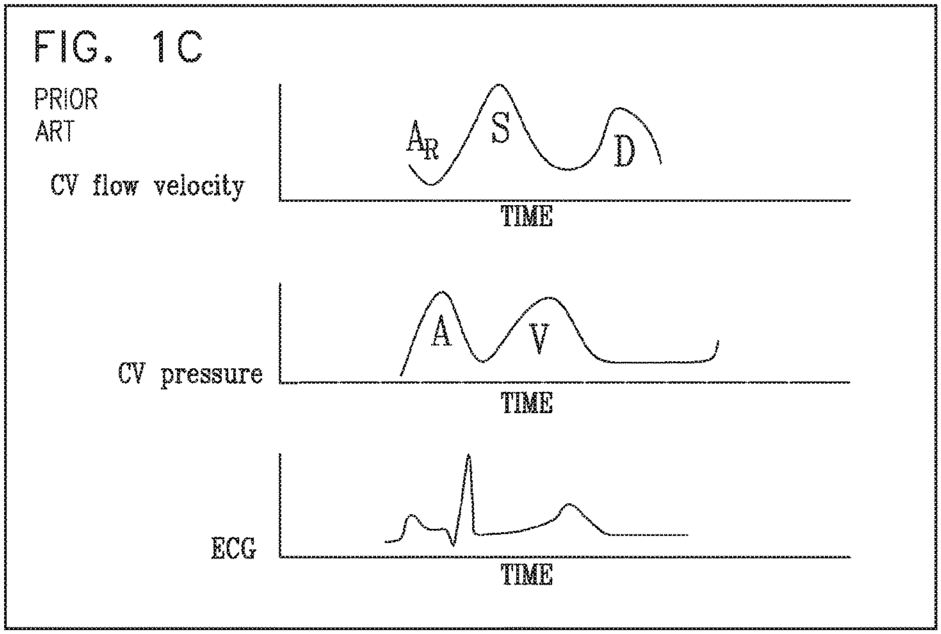
FIG. 1C is a set of graphs showing a healthy subject's central venous flow velocity profile and central venous pressure profile with respect to the subject's ECG cycle.

FIG. 1C is a set of graphs showing the central venous flow velocity profile and central venous pressure profile of a healthy subject with respect to the subject's ECG cycle. The flow velocity profile is characterized by biphasic forward flow (i.e., forward flow during both systole (S) and diastole (D)), with flow during systole being greater than that during diastole. Typically, there is a small amount of reverse flow AR, during atrial contraction. The central venous pressure profile is characterized by relatively low pressure over the duration of the cardiac cycle, with the A-wave (i.e., the pressure during atrial contraction), typically being greater than the V-wave (i.e., the pressure during systole).

Figure 2A:
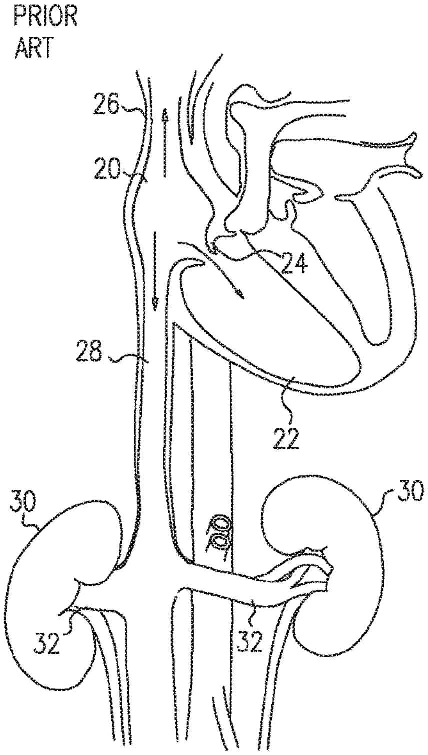
FIGS. 2A-B are schematic illustrations of the right heart of a subject suffering from congestive heart failure, during diastole and systole respectively.
Figure 2B:
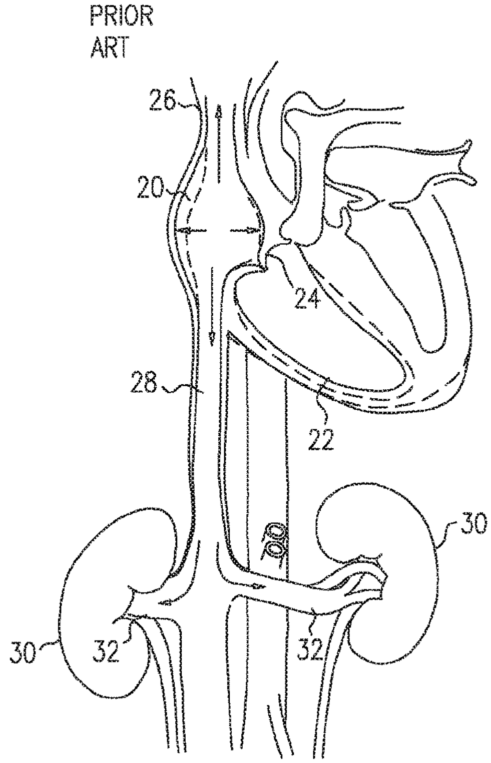

Reference is now made to FIGS. 2A-B, which are schematic illustrations of the heart of a subject suffering from congestive heart failure, during diastole and systole respectively. As shown in FIG. 2A, as with the healthy heart, during diastole, blood flows from the subject's right atrium 20 to the subject's right ventricle 22. As shown in FIG. 2B, during systole, due to right atrial pressure being too high, filling of the subject's right atrium is cut short, causing there to be an increase in pressure in the superior vena cava 26, and/or the inferior vena cava 28, as the high atrial pressure is transmitted to the vena cava. In some cases (e.g., in cases of very high right atrial pressure, tricuspid regurgitation, or atrial fibrillation), there may be retrograde flow of blood from the right atrium into the superior vena cava 26, the inferior vena cava 28, and/or tributaries of the vena cava, due to the filling of the right atrium being cut short.

Figure 2C:
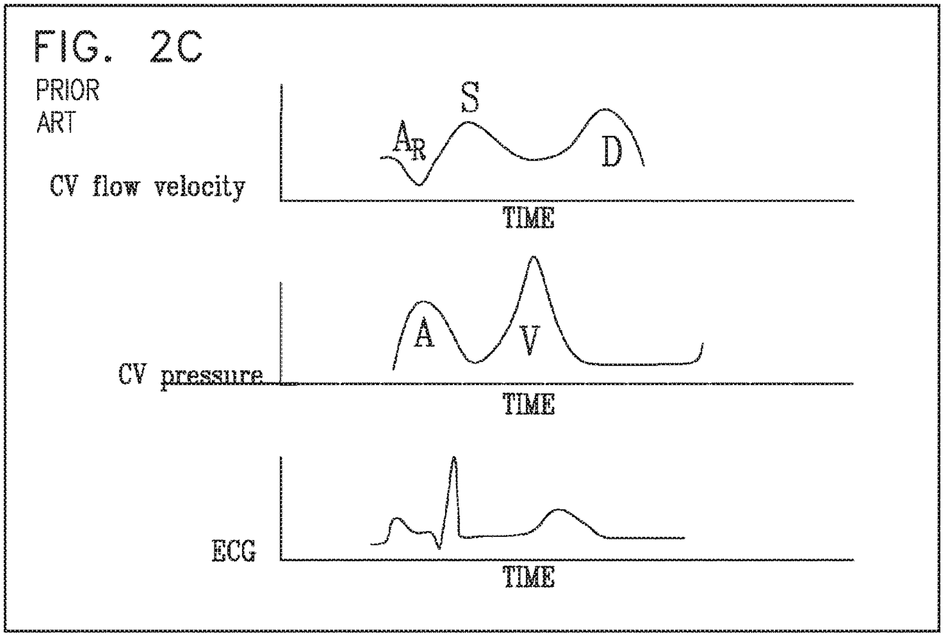
FIG. 2C is a set of graphs showing the central venous flow velocity profile and central venous pressure profile of the subject suffering from congestive heart failure, with respect to the subject's ECG cycle.

FIG. 2C is a set of graphs showing the central venous flow velocity profile and central venous pressure profile of the subject suffering from congestive heart failure, with respect to the subject's ECG cycle. The flow velocity profile is characterized by increased retrograde flow AR at the end of diastole, and by antegrade flow during systole being less than that during diastole. For example, in some subjects there is zero flow, or reverse flow during systole. The central venous pressure profile is characterized by relatively high pressure over the duration of the cardiac cycle with the V-wave being particularly high relative to that of a healthy heart, and relative to the subject's A-wave.

Figure 3A:
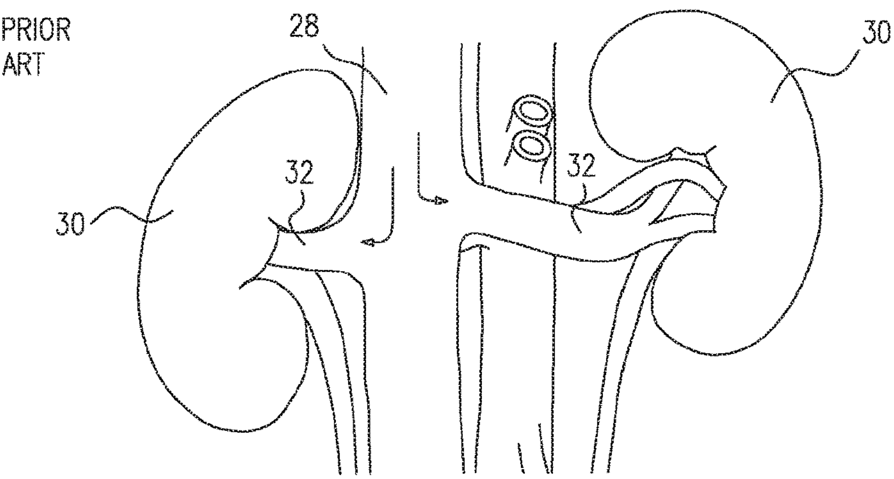
FIG. 3A is a schematic illustration of blood flowing back toward the kidneys of a subject suffering from congestive heart failure.
Figure 3B:
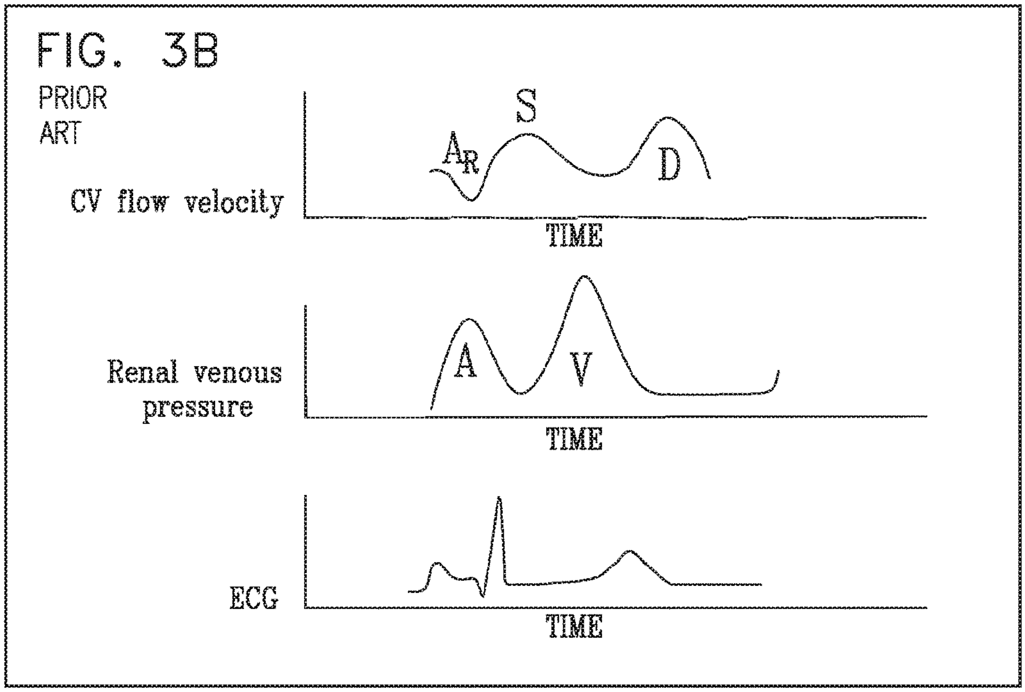
FIG. 3B is a set of graphs showing the central venous flow velocity profile and renal vein pressure profile of the subject suffering from congestive heart failure, with respect to the subject's ECG cycle.

Reference is now made to FIG. 3A, which is a schematic illustration of blood flowing back toward the kidneys 30 of a subject suffering from congestive heart failure, via the subject's left and right renal veins 32. FIG. 3B is a set of graphs showing the central venous flow velocity profile and renal vein pressure profile of the subject suffering from congestive heart failure, with respect to the subject's ECG cycle. It is noted that the graphs shown in FIG. 3B are the same as those shown in FIG. 2C, except that the pressure profile shown in FIG. 3B is that of the renal vein, whereas the pressure profile shown in FIG. 2C is the central venous pressure profile. As shown, typically, in the absence of a device placed in the renal vein (as performed, in accordance with some applications of the present invention), and assuming that the renal vein is at the same height as the central venous system, the renal venous pressure profile is identical to the central venous pressure profile. The renal vein pressure profile is characterized by relatively high pressure over the duration of the cardiac cycle, with the V-wave being particularly high relative to that of a healthy heart.

Figure 4A:
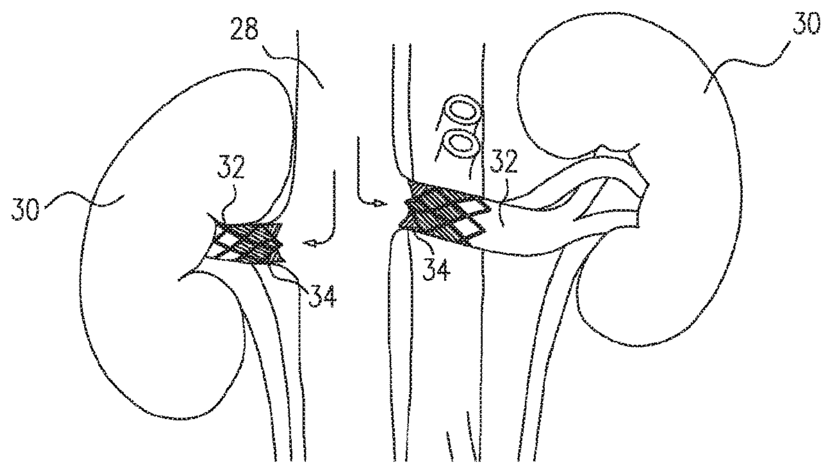
FIG. 4A is a schematic illustration of prosthetic valves placed in left and right renal veins of a subject suffering from congestive heart failure, in accordance with some applications of the present invention.
Figure 4B:
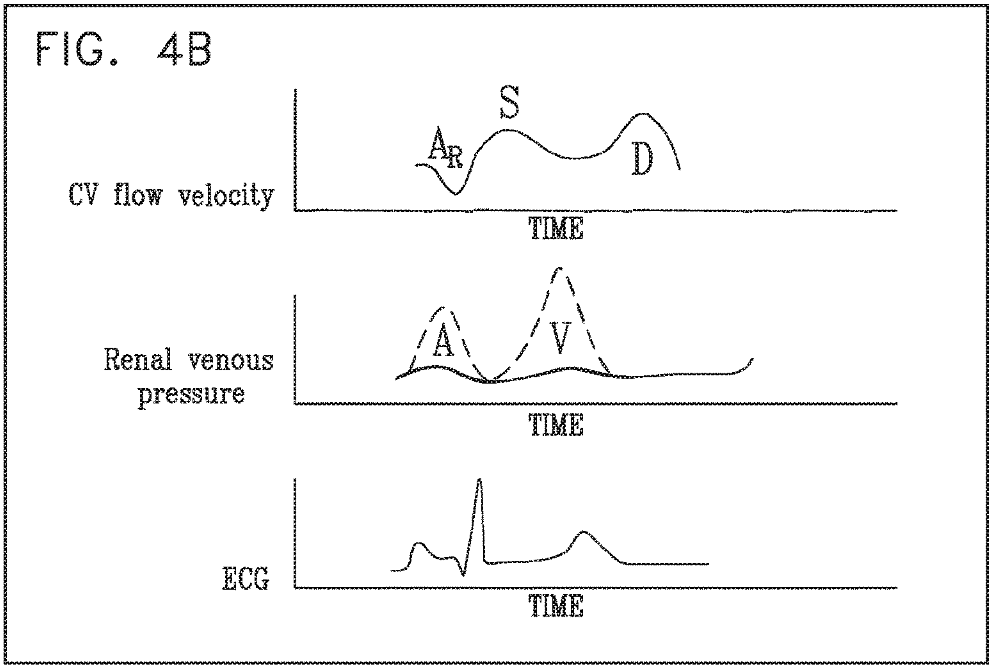
FIG. 4B is a set of graphs showing the central venous flow velocity profile and renal vein pressure profile of the subject suffering from congestive heart failure, with respect to the subject's ECG cycle, subsequent to placement of prosthetic valves in the subject's left and right renal veins, in accordance with some applications of the present invention.

Reference is now made to FIG. 4A, which is a schematic illustration of prosthetic valves 34 placed in left and right renal veins 32 of a subject suffering from congestive heart failure, in accordance with some applications of the present invention. The valves protect the renal vein from pressure increases resulting from high central venous pressures, by the valves closing in response to pressure within the vena cava being greater than a threshold pressure. Alternatively or additionally, the valves reduce pressure at the subject's kidneys 30 by reducing the back flow of blood toward the kidneys via the renal veins (e.g., during atrial contraction, AR, or any other phase where there may be retrograde blood flow in the inferior vena cava), by the valves closing in response to blood flowing back into the renal veins. FIG. 4B is a set of graphs showing the central venous flow velocity profile and renal vein pressure profile of the subject suffering from congestive heart failure, with respect to the subject's ECG cycle, subsequent to placement of prosthetic valves 34 in the subject's left and right renal veins 32. On the graph showing the renal venous pressure profile, the central venous pressure is indicated by a dashed curve. As shown, placement of the valves in the veins causes a lowering of the renal vein pressure profile, even though the subject's central venous pressure is elevated. In particular, placement of the valves causes a lowering of the V-wave (i.e., the pressure during systole).

The inventor of the present application hypothesizes that by reducing pressure at the kidneys, placement of a valve inside a renal vein, causes an improvement of renal function and/or prevention or a reduction in deterioration of the subject's renal function. Typically, placement of a valve inside a renal vein reduces renal venous and interstitial pressure, thereby causing a decrease in parenchymal ischemia and injury, and/or an increase in renal blood flow, glomerular filtration rate, and/or in erythropoetin production. For some applications, placement of a valve inside a renal vein improves the subject's cardiac function, e.g., by reducing afterload. For some applications, placement of a valve inside a renal vein improves the subject's renal function and/or cardiac function, e.g., by causing improved renal salt and water excretion, by suppressing renin-angiotensin-aldosterone system (RAAS) activation, by suppressing arginine-vasopressin system activation, and/or by suppressing the sympathetic nervous system. For some applications, placement of a valve inside a renal vein treats anemia of the subject, by improving the subject's renal function.

Valve 34 is typically placed inside one or both of the subject's renal veins in order to provide acute treatment to a subject suffering from cardiac dysfunction, congestive heart failure, low renal blood flow, high renal vascular resistance, arterial hypertension, and/or kidney dysfunction. In accordance with respective applications, valve 34 is permanently implanted in left and/or right renal vein 32 or is temporarily (e.g., retrievably) placed within the renal vein. For example, the valve may be placed in a renal vein for a period of more than 12 hours (e.g., more than 24 hours), and/or less than three months (e.g., less than one month), during which the subject is undergoing an acute episode of heart failure, and subsequently, the valve may be retrieved from the renal vein. Or, valve 34 may be permanently implanted in left and/or right renal vein 32 in order to provide chronic treatment to a subject suffering from cardiac dysfunction, congestive heart failure, low renal blood flow, high renal vascular resistance, arterial hypertension, and/or kidney dysfunction. For some applications, a course of treatment is applied to a subject over several weeks, several months, or several years, in which the valves are intermittently placed inside the subject's left and/or right renal vein, and the subject is intermittently treated in accordance with the techniques described herein. For example, the subject may be intermittently treated at intervals of several days, several weeks, or several months.

Typically, valve 34 is placed inside one or both of the subject's renal veins in order to provide treatment to a subject suffering from elevated central venous pressure relative to central venous pressure of a healthy subject. The valve is configured to reduce the subject's renal venous pressure relative the subject's elevated central venous pressure. For some applications, the valve is placed inside the renal vein of a subject in response to the subject's renal venous pressure being elevated relative to that of a healthy subject, the subject's elevated renal venous pressure being substantially due to the subject suffering from elevated central venous pressure. For some applications, the valve is placed in the subject's renal vein in response to the subject's central venous pressure being elevated relative to that of a healthy subject, even though the subject is not suffering from a condition that causes renal venous pressure to be elevated due to pressure being exerted on the renal vein through the walls of the renal vein from a location outside the renal vein (e.g., as in the case of a subject suffering from nutcracker syndrome). For some applications, the valve is placed inside the renal vein of a subject in response to the subject's central venous pressure being elevated relative to that of a healthy subject and even though the subject is not suffering from tricuspid valve regurgitation. The valve is typically configured to be placed in the subject's renal vein in order to treat the subject, even in the absence of any other device being placed outside the subject's venous system and within the subject's abdomen (e.g., around the outside of the subject's renal vein).

Figure 5:
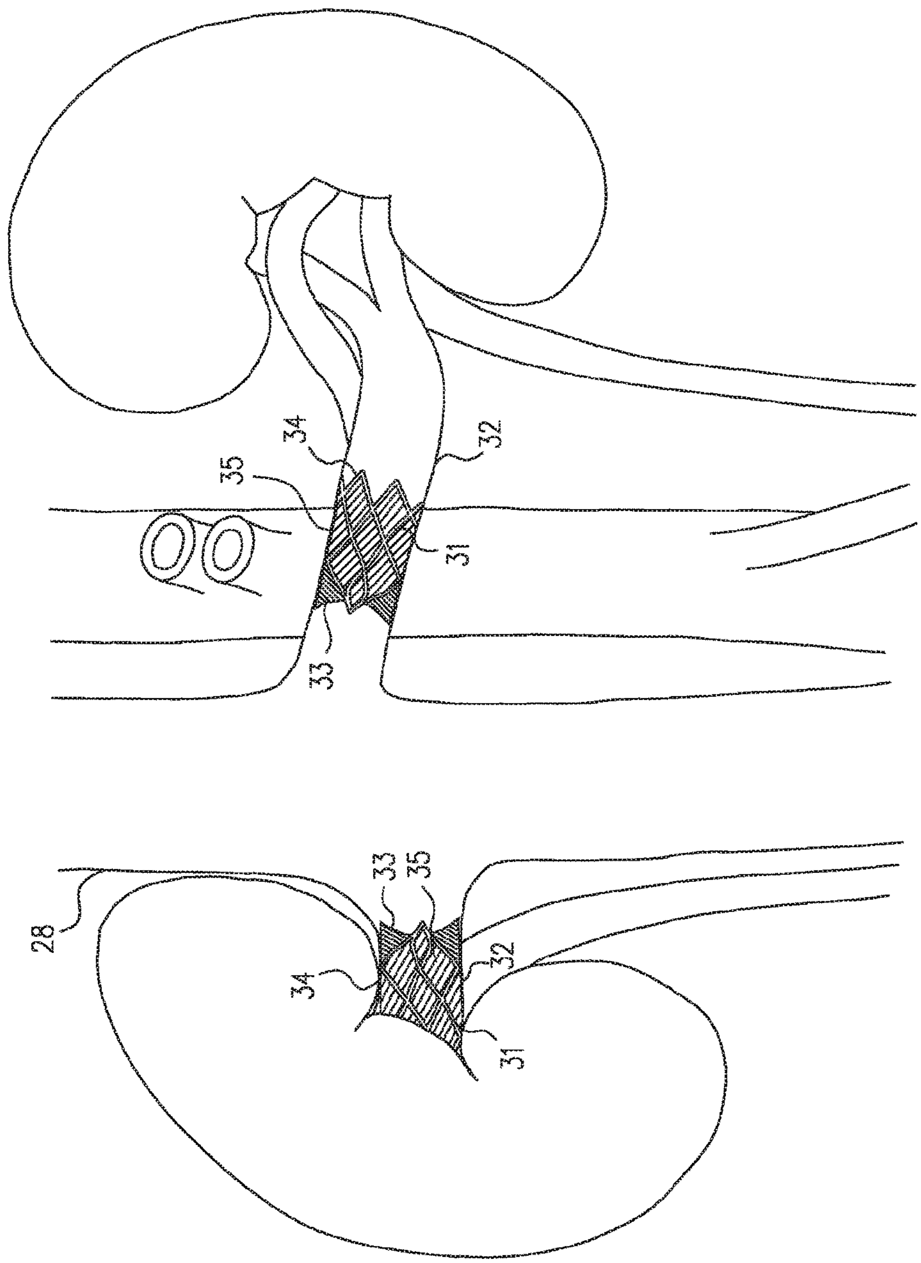
FIG. 5 is a schematic illustration of prosthetic valves that are placed in a subject's left and/or right renal veins, in accordance with some applications of the present invention.

Reference is now made to FIG. 5, which is a schematic illustration of prosthetic valves 34 that are placed in a subject's left and right renal veins 32, in accordance with some applications of the present invention.

It is noted that for some applications, a valve is placed in only one of the left or the right renal veins. For some applications, more than one valve is placed in one or both of the left and right renal veins. For example, a first valve may be placed in the main branch of the renal vein that is a direct tributary of the vena cava, and a second valve may be placed in an upstream branch of the renal vein that is closer to the kidney, and is a tributary of the main renal vein. For some applications, three or more valves are placed in respective renal veins of a subject who has multiple renal veins.

Typically, the valve that is placed in the renal vein includes a frame 31 (e.g., a frame that is made of nitinol, stainless steel, cobalt chromium, platinum iridium (or other non-absorbable metals), magnesium (or other absorbable metals), a polymer, and/or a different material). Further typically, the valve includes prosthetic valve leaflets 33 (e.g., leaflets made from complete or partial venous valves harvested from calves, pigs, sheep, horses, marsupials, or other animals; leaflets made from pericardial tissue, from small intestinal submucosa from pigs or other animals, and/or from a synthetic material, such as polyester, polyurethane, any other polymer, and/or any thin and flexible material (e.g., material generated by electrospinning, or sputter deposition, including thin-film nitinol leaflets)). Still further typically, the valve includes sealing material 35, which is coupled to (e.g., sutured to) the valve frame, and that seals the valve frame with respect to the walls of the renal vein. For some applications, a similar material is used for sealing material 35 as is used for prosthetic valve leaflets 33. The frame supports the prosthetic valve leaflets, e.g., by the prosthetic valve leaflets being sutured to the frame. Typically, the valve frame is a non-branched valve frame. For example, the frame may define a generally cylindrical portion thereof, the frame not defining additional cylindrical portions that branch from the generally cylindrical portion. Thus, typically, the valve frame defines a single longitudinal axis thereof, the longitudinal axis being a generally straight line along a full length of the frame.

Typically, the prosthetic valve is configured such that the valve leaflets close in response to pressure within the vena cava being greater than a threshold pressure, and/or in response to retrograde blood flow through the renal veins exerting pressure on the downstream sides of the prosthetic valve leaflets. In the closed state of the valve, the valve leaflets, in a passive manner (i.e., without requiring external energy to be supplied to the device (e.g., from a power supply or a battery)), reduce venous pressure within the renal vein relative to central venous pressure of the subject.

Typically, the prosthetic valve is configured such that the valve leaflets open in response to antegrade blood flow through the renal vein, from the kidney to the vena cava, exerting pressure on the upstream sides of the prosthetic valve leaflets. Further typically, the valve leaflets are configured to open in response to a pressure of less than 6 mmHg (e.g., less than 3 mmHg) being exerted on the upstream sides of the prosthetic valve leaflets. For some applications, the valve leaflets are configured to open in response to antegrade blood flow through the vena cava, due to the fluid flow dynamics of the antegrade blood flow in the vicinity of the downstream sides of the prosthetic valve leaflets. In the open state of the valve, the valve leaflets typically allow generally unimpeded antegrade blood flow therethrough. For some applications, the prosthetic valve frame is shaped such as to deform a shape of a vessel wall in the vicinity the downstream sides of the prosthetic valve leaflets, such as to enhance the aforementioned fluid flow dynamics, as described in further detail hereinbelow.

It is noted that, when used in the present application to refer to locations within a subject's veins, the term "upstream" is used to denote a location that is further from the subject's right atrium, and the term "downstream" is used to refer to a location that is closer the subject's right atrium. Thus, blood typically flows from upstream locations to downstream locations. When used in the present application to refer to a portion of a device, the term "upstream" is used to denote an end or side of the device (or a portion thereof) which, subsequent to the device being deployed, will typically be at an upstream location within the vein relative to another end or side of the device. When used in the present application to refer to a portion of a device, the term "downstream" is used to denote an end or side of the device (or a portion thereof) which, subsequent to the device being deployed, will typically be at a downstream location within the vein relative to another end or side of the device.

Typically, a valve (e.g., valve 34) is placed inside renal vein 32, such that the valve leaflets are disposed inside the renal vein. Alternatively, a valve is placed within the subject's vena cava such that valve leaflets are disposed in the vicinity of the ostium at the junction of the renal vein with the vena cava. For example, a valve frame may be anchored to the vena cava with the valve leaflets coupled to the valve frame, such that the valve leaflets are disposed in the vicinity of the ostium at the junction of the renal vein with the vena cava, e.g., as described hereinbelow with reference to valves 110 and 120, shown in FIGS. 12A-B. In such applications, the valve leaflets are configured to open in response to antegrade blood flow from the renal vein into the vena cava and to close in response to retrograde flow from the vena cava into the renal vein. Thus, for such applications, the valve occludes the renal vein from retrograde blood flow from the vena cava selectively with respect to the subject's central venous system.

Figure 11:
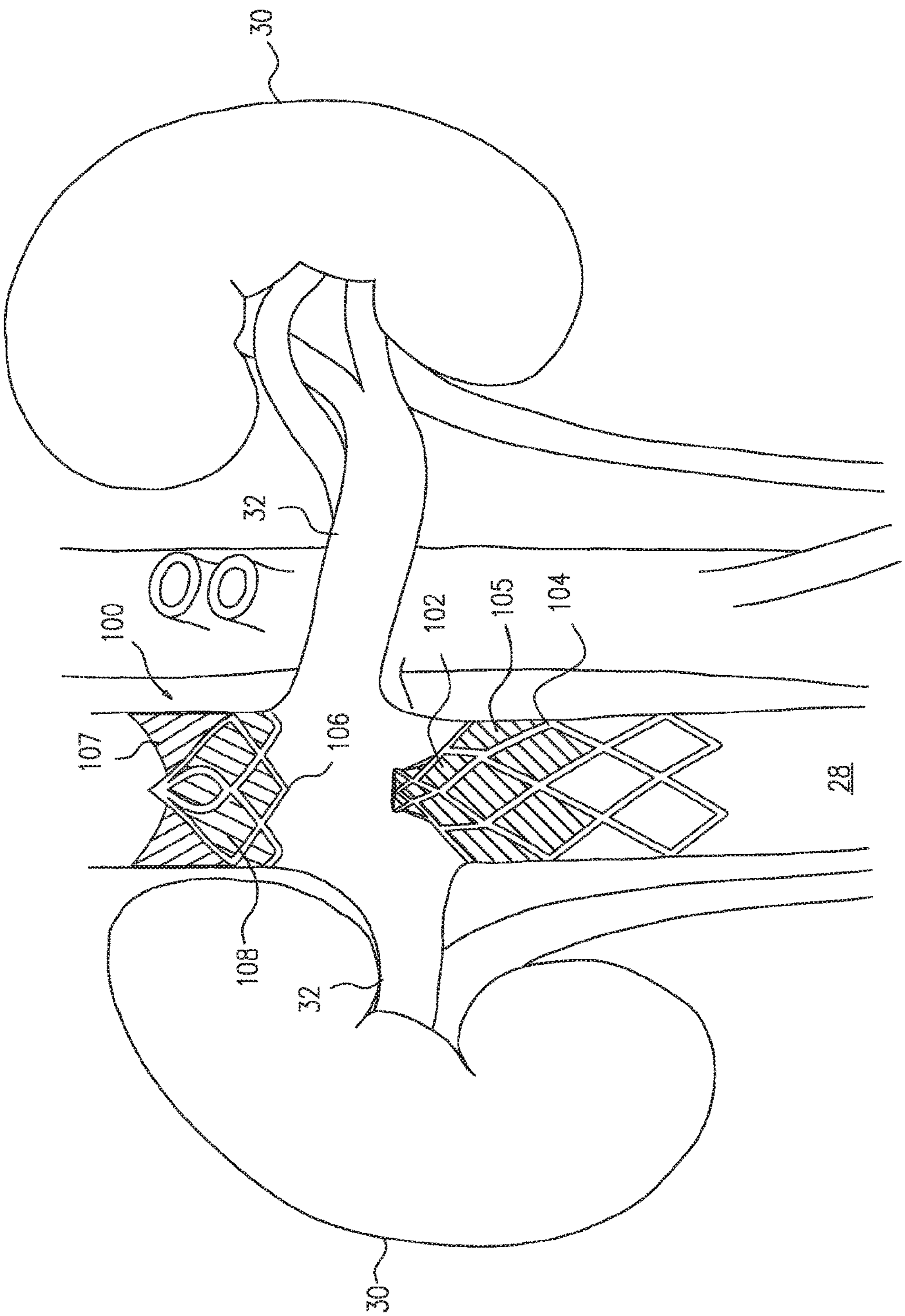
FIG. 11 is a schematic illustration of a nozzle and a valve disposed in a subject's vena cava, in accordance with some applications of the present invention.

For some applications, as an alternative to, or in addition to, placing a valve (e.g., valve 34) in renal vein 32 or placing a valve such as valve 110 or valve 120 in the vena cava, a prosthetic valve is placed in inferior vena cava 28, valve leaflets of the valve being configured such that the valve leaflets (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets. For example, valve 100 described hereinbelow with reference to FIG. 11 is configured such that the valve leaflets thereof function in the described manner.

It is noted that placing the valve in the inferior vena cava in the above-described manner (e.g., as described with reference to FIG. 11) may result in an increase in right atrial pressure by shutting off the compliant system of lower body veins that helps dampen the right atrial pressure, which may lead to venous congestion of the upper body. This may be because closure of the valve leaflets causes blood flow through the inferior vena cava itself to be occluded. By contrast, by placing the valve leaflets inside the renal vein, or by placing the valve leaflets in the vicinity of the ostium of the junction of the renal vein with the vena cava, even when the valve leaflets are closed, flow through the vena cava is not occluded. Therefore, typically, a prosthetic valve is not placed in inferior vena cava 28, in a manner that the valve leaflets (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets. Rather, a valve is typically placed inside the renal vein, or inside the vena cava such that the valve leaflets are disposed in the vicinity of the ostium of the junction of the renal vein with the vena cava, and such that the valve leaflets are configured to open in response to antegrade blood flow from the renal vein into the vena cava and to close in response to retrograde flow from the vena cava into the renal vein. Even in the closed state of the valve leaflets of such a valve, the valve leaflets do not occlude blood flow through the vena cava itself. Thus, such valves typically do not shut off the compliant system of lower body veins that helps dampen the right atrial pressure.

It is further noted that, by placing the valve in the renal vein, or inside the vena cava, such that the valve leaflets are disposed in the vicinity of the ostium of the junction of the renal vein with the vena cava, retrograde blood flow to the kidney may be reduced by the valve even during exercise, and/or other physical activity of the subject's body, during which there is typically increased flow and pressure in the inferior vena cava that is generated by venous return from veins of the subject's legs. By contrast, a valve placed in the inferior vena cava such that the valve leaflets (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets, may not reduce pressure in the renal vein during exercise, and/or other physical activity of the subject's body, during which there is typically increased flow and pressure in the inferior vena cava that is generated by venous return from veins of the subject's legs. This is because, under such circumstances, a valve that is implanted in the inferior vena cava, and the leaflets of which are configured as described, will typically remain open in response to the increased flow and pressure at the inferior vena cava.

Furthermore, if a valve is placed in the inferior vena cava downstream of the junction that the renal vein makes with the inferior vena cava and such that the valve leaflets (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets (e.g., valve 100 shown in FIG. 11), then the valve will not protect the renal vein from retrograde blood flow into the renal vein, or from high venous pressures being transmitted to the renal vein from blood that is supplied to the inferior vena cava by the venous system of the lower body. Therefore, typically, at least one valve is placed in one of the renal veins, or inside the vena cava such that the valve leaflets are disposed in the vicinity of the ostium of the junction of the renal vein with the vena cava, valve leaflets of the valve being configured to open in response to antegrade blood flow from the renal vein into the vena cava and to close in response to retrograde flow from the vena cava into the renal vein. Further typically, a prosthetic valve is not placed in inferior vena cava 28, such that the valve leaflets (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets.

Figure 6A:
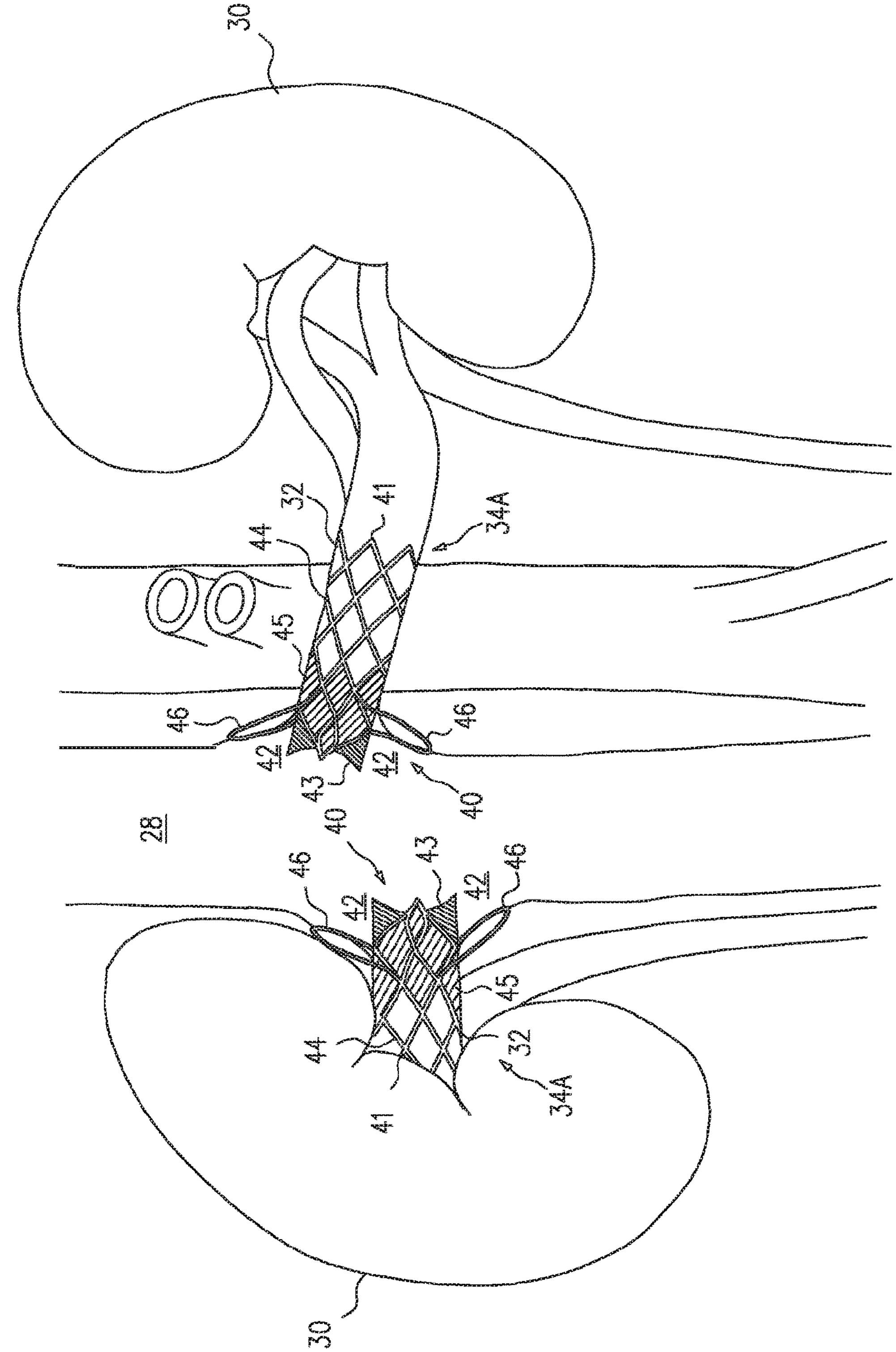
FIGS. 6A-D are schematic illustrations of prosthetic valves that are configured to be placed at a junction of a subject's renal vein and the subject's vena cava, such as to form a cavity at the junction, in accordance with some applications of the present invention.
Figure 6B:
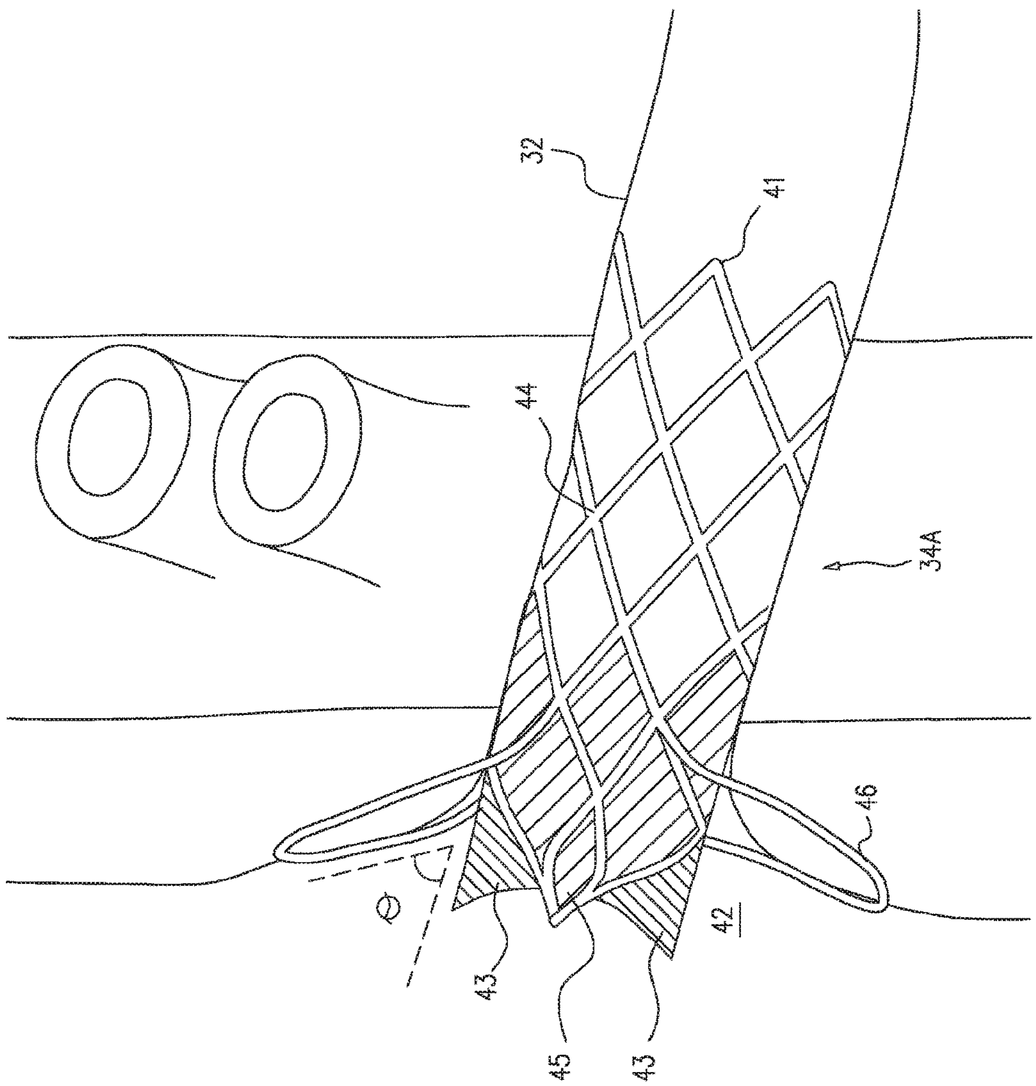
Figure 6C:
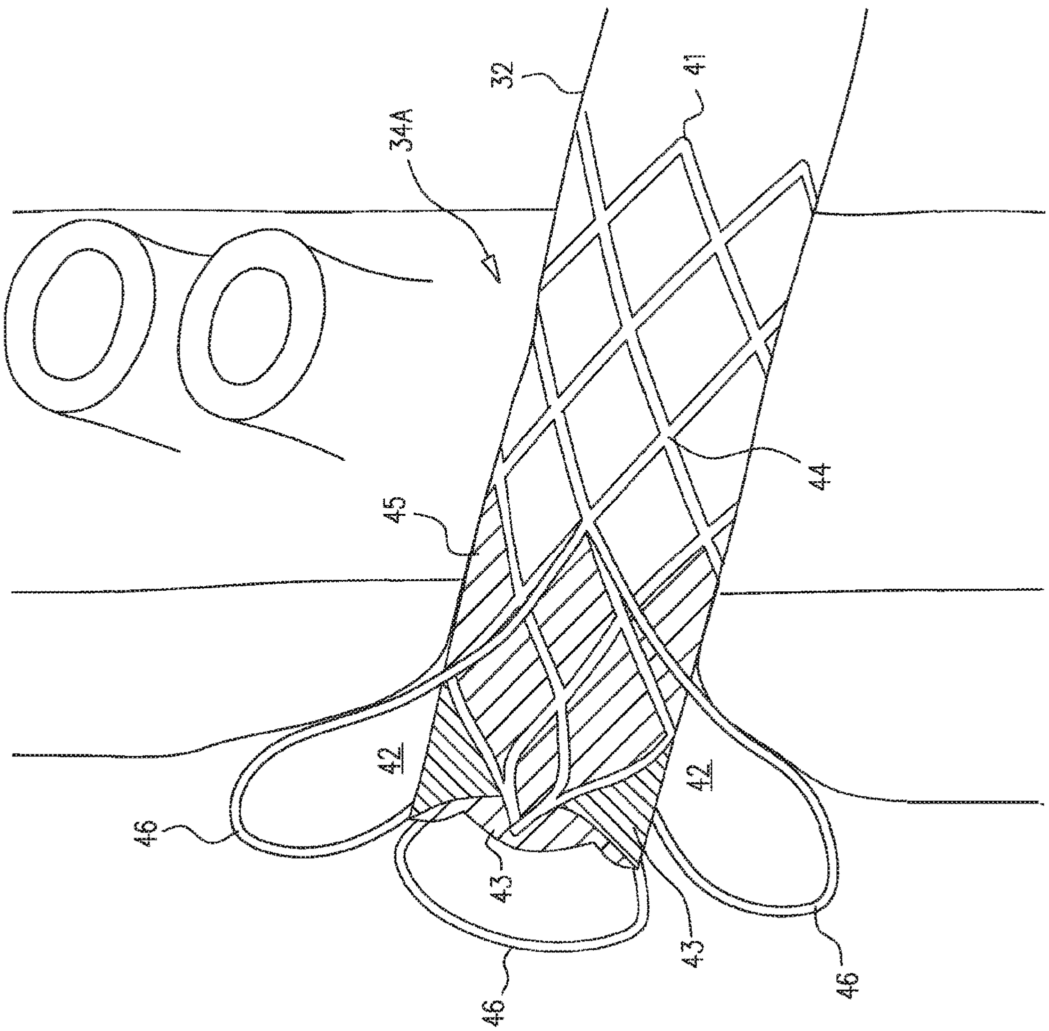

Reference is now made to FIGS. 6A-C, which are schematic illustrations of prosthetic valves 34A that are configured to be placed at a junction 40 of a subject's left and/or right renal vein 32 and the subject's vena cava 28, such as to form a cavity 42 at the junction, in accordance with some applications of the present invention. Valves 34A are an example of prosthetic valve 34 described hereinabove with reference to FIGS. 4A-B.

Typically, valve 34A includes a frame 41 (e.g., a frame that is made of nitinol, stainless steel, cobalt chromium, platinum iridium (or other non-absorbable metals), magnesium (or other absorbable metals), a polymer, and/or a different material). Further typically, the valve includes prosthetic valve leaflets 43 (e.g., leaflets made from complete or partial venous valves harvested from calves, pigs, sheep, horses, marsupials, or other animals; leaflets made from pericardial tissue, from small intestinal submucosa from pigs or other animals, and/or from a synthetic material, such as polyester, polyurethane, any other polymer, and/or any thin and flexible material (e.g., material generated by electrospinning, or sputter deposition, including thin-film nitinol leaflets)). Still further typically, the valve includes sealing material 45, which is coupled to (e.g., sutured to) the valve frame, and that seals the valve frame with respect to the walls of the renal vein. For some applications, a similar material is used for sealing material 45 as is used for prosthetic valve leaflets 43. The frame supports the prosthetic valve leaflets, e.g., by the prosthetic valve leaflets being sutured to the frame.

For some applications, valve frame 41 is shaped to define a generally cylindrical portion 44, the prosthetic valve leaflets being coupled to a downstream portion of the generally cylindrical portion. At least one protruding portion 46 protrudes radially from the generally cylindrical portion of the valve frame. Typically the protruding portion diverges radially from the outer surface of the cylindrical portion of the valve frame, such that the separation between the protruding portion and the outer surface of the cylindrical portion of the frame is greater at the downstream end of the protruding portion than at the upstream end of the protruding portion.

For some applications, the prosthetic valve is placed at junction 40, such that protruding portion 46 deforms at least a portion of the junction, such as to form a cavity 42 at the junction. Typically, the prosthetic valve leaflets are coupled to the valve frame such that the valve leaflets are disposed at least partially (and typically, fully) downstream of the downstream end of the protruding portion. Thus, when the valve is placed at junction 40, the valve leaflets are typically disposed within the cavity that is formed at the junction by the protruding portion. Typically, the valve frame is shaped such that, when the valve is placed at junction 40, the protruding portion forms a cavity that generates blood flow at the valve leaflets that is such as to prevent blood from stagnating in the vicinity of the valve leaflets.

For some applications, the valve frame is shaped such that, when the valve is placed at junction 40, the protruding portion forms a cavity that is such as to cause blood flow in the vicinity of the downstream side of the valve leaflets to exert pressure on the valve leaflets, such that the valve leaflets close, or move closer together to facilitate closing. Alternatively, the valve frame is shaped such that, when the valve is placed at junction 40, the protruding portion forms a cavity that is such as to cause antegrade blood flow to accelerate in the vicinity of the downstream side of the valve leaflets, thereby causing (or enhancing) opening of the leaflets.

For some applications, valve frame 41 defines a single protruding portion 46. For some applications, the single protruding portion is disposed around the full circumference of the valve frame. Alternatively, the valve frame defines two or more (e.g., two, three, or four) protruding portions that protrude from generally cylindrical portion 44 of the valve frame. As shown in FIG. 6B, each of the protruding portions forms an angle theta with respect to the outer surface of the downstream portion of the cylindrical portion of the valve frame. Typically, angle theta is greater than 20 degrees. Further typically, angle theta is greater than 40 degrees, e.g., greater than 50 degrees. For some applications, angle theta is less than 90 degrees, e.g., less than 70 degrees. For some applications, angle theta is 90 degrees.

For some applications, valve frame 41 defines generally cylindrical portion 44, and at least one protruding portion 46 (e.g., a plurality of protruding portions), the generally cylindrical portion and the protruding portion being reversibly couplable to one another. Typically, the valve leaflets are coupled to the generally cylindrical portion, as described hereinabove. The at least one protruding portion is couplable to the cylindrical portion such that when the protruding portion is coupled to the cylindrical portion, the protruding portion protrudes radially from the cylindrical portion, as described hereinabove. For some applications, the protruding portion is implanted within the renal vein separately from the cylindrical portion. For example, the protruding portion may first be placed in the renal vein, and, subsequently, the cylindrical portion may be placed within the renal vein and coupled to the protruding portion.

For some applications of the invention, the valve leaflets of the prosthetic valve are replaced, subsequent to the valve having been placed in the subject's renal vein (e.g., in the event of fatigue of the valve leaflets). In order to replace the prosthetic valve leaflets, the cylindrical portion of the valve frame is decoupled from the protruding portion of the valve frame. The cylindrical portion is removed from the subject's body, and the protruding portion is left inside the subject's vein. Subsequently, a replacement cylindrical portion (or the same cylindrical portion with new prosthetic leaflets coupled thereto) is placed inside the renal vein and coupled to the protruding portion.

For some applications, valve frame 41 defines generally cylindrical portion 44, and at least one protruding portion 46 (e.g., a plurality of protruding portions), the cylindrical portion and the protruding portion being irreversibly coupled to one another, and/or being formed as a single integrated structure.

Figure 7A:
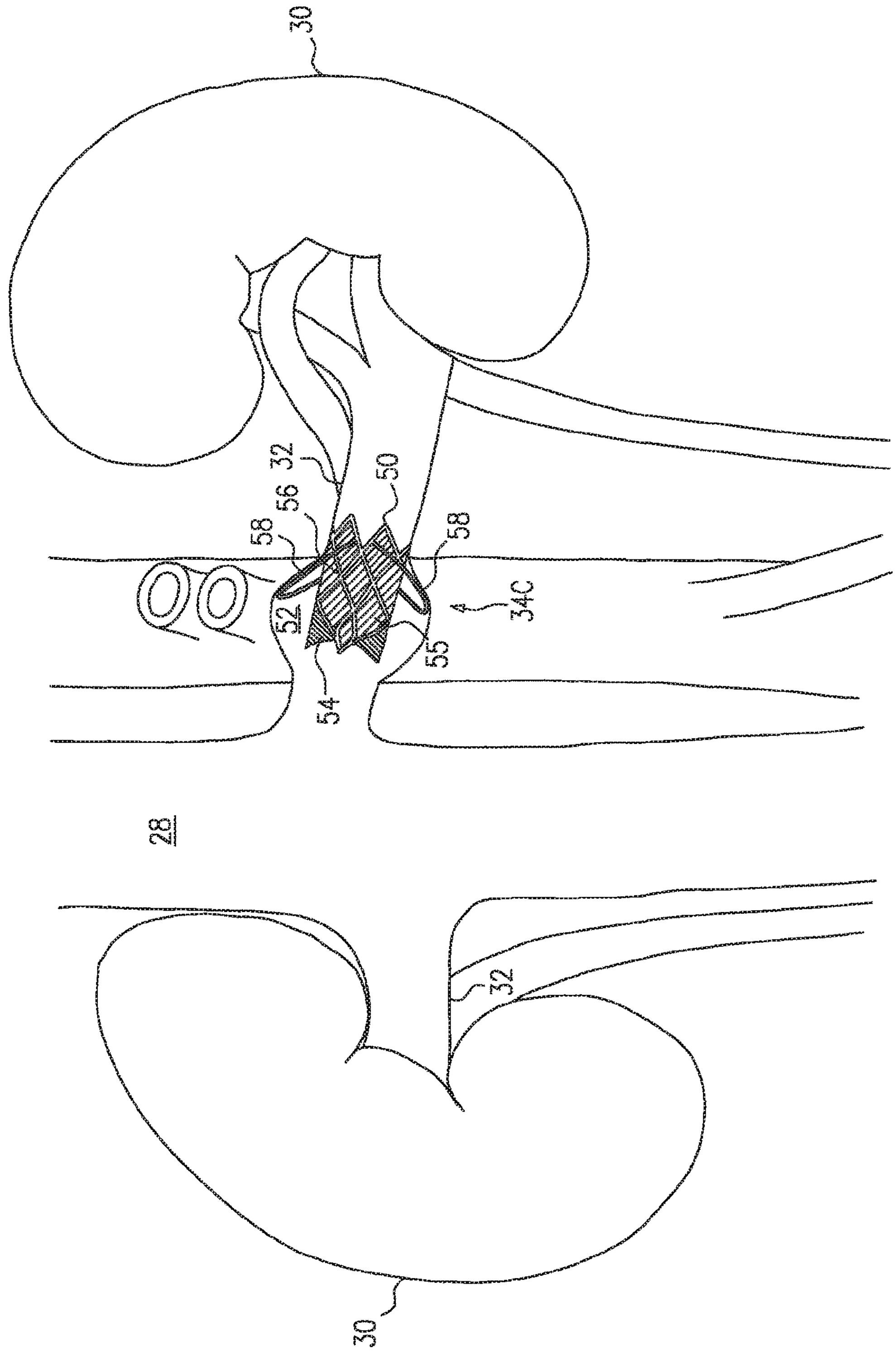
FIGS. 7A-F are schematic illustrations of prosthetic valves that are configured to be placed inside the subject's renal vein, frames of the valves being configured to cause the vein to form a bulged portion around the valve leaflets of the valves, in accordance with some applications of the present invention.

As described hereinbelow with reference to valve 34C (shown in FIGS. 7A-C), prosthetic valve leaflets 43 of valve 34A are typically coupled to valve frame 41 such that an upstream end of each of the prosthetic valve leaflets is longitudinally spaced from a downstream end of the at least one protruding portion 46. Thus, when the valve is placed at junction 40, the valve leaflets are typically disposed within the cavity that is formed at the junction, and the valve leaflets are not surrounded by any portion of the valve frame. Thus, even if the protruding portion of the valve frame is rigid or partially rigid, damage to the valve leaflets that may be caused during opening of the valve leaflets, by the valve leaflets impacting the rigid or semi-rigid protruding portion, is prevented.

Alternatively, prosthetic valve leaflets 43 of valve 34A may be coupled to valve frame 41 such that an upstream end of each of the prosthetic valve leaflets is upstream of at least a portion of the at least one protruding portion 46. For some applications, protruding portions 46 are shaped and/or sized to be disposed outside of radial projections of downstream edges of the valve leaflets, such that when the prosthetic valve leaflets are fully opened, the leaflets do not impact any rigid or partially rigid portions of the protruding portions. For example, as shown in FIG. 6C, the protruding portions may be shaped such that any rigid or partially rigid portions of the protruding portions are disposed around the outsides of the downstream edges of the prosthetic valve leaflets even when the valve leaflets are in fully-open states thereof. Thus, when the prosthetic leaflets are opened, the prosthetic leaflets may impact the vessel wall, but do not impact any rigid or partially rigid portions of the protruding portions.

Figure 6D:
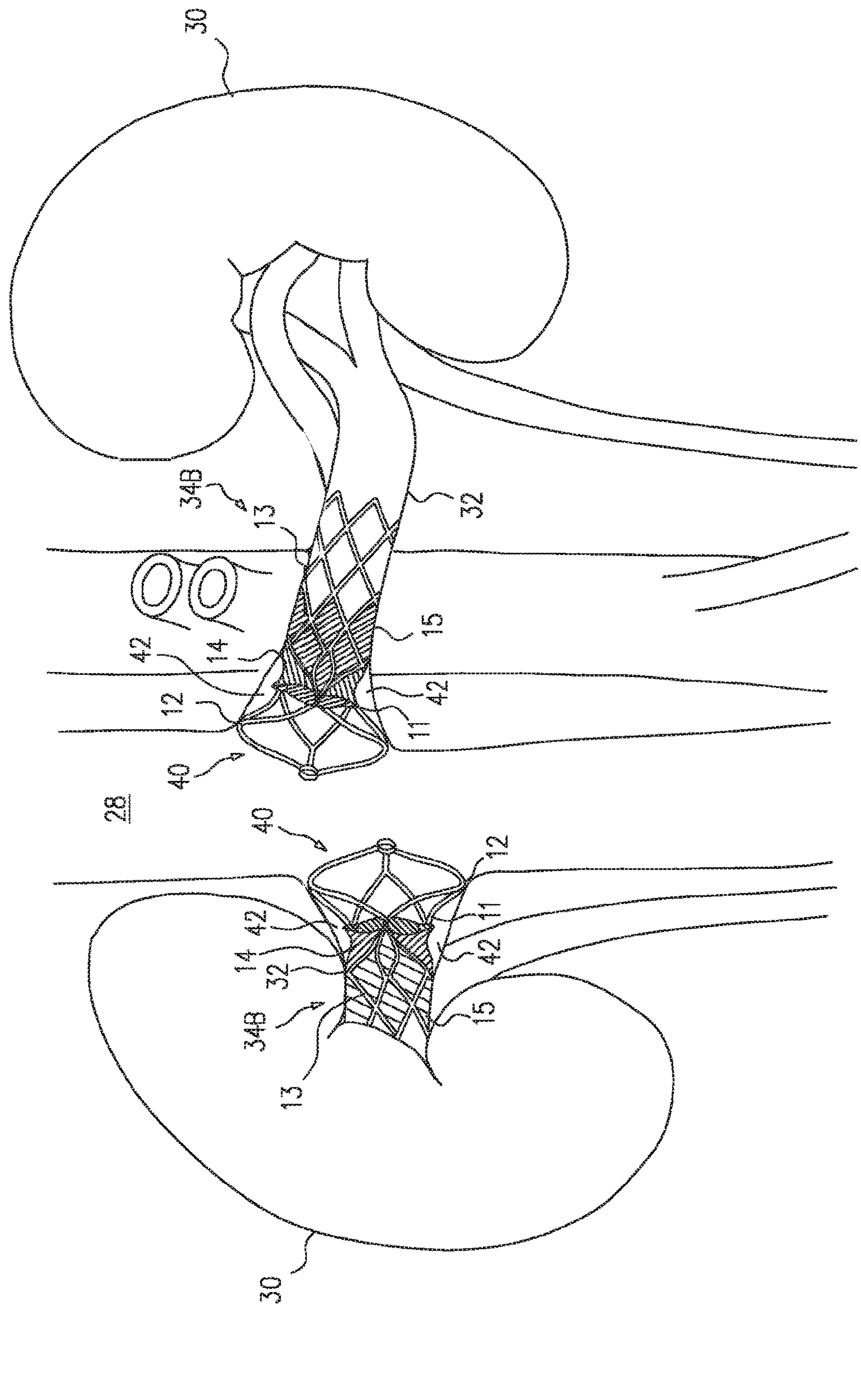

Reference is now made to FIG. 6D, which is a schematic illustration of a prosthetic valve 34B that is configured to be placed at a junction 40 of a subject's renal vein 32 and the subject's vena cava 28, such as to form a cavity 42 at the junction, in accordance with some applications of the present invention. Valve 34B is an example of prosthetic valve 34 described hereinabove with reference to FIGS. 4A-B. Valve 34B is generally similar to valve 34A described hereinabove with reference to FIGS. 6A-C, except that, rather than defining protruding portions that form a cavity at junction 42 (as described with reference to valve 34A, shown in FIGS. 6A-C), frame 11 of valve 34B is shaped to define a bulging portion 12 thereof that is configured to form a cavity at junction 42.

Typically, frame 11 of valve 34B includes a relatively narrow portion 13 thereof to which valve leaflets 14 are coupled. Further typically, a sealing material 15 is coupled to the narrow portion of the valve frame, the sealing material being configured to seal the valve frame with respect to the walls of the renal vein. The valve leaflets and the sealing material are generally as described hereinabove. Bulging portion 12 of frame 11 of valve 34B is typically disposed downstream with respect to the narrow portion of the valve frame and is bulged with respect to the narrow portion. Bulging portion 12 is configured to form a cavity at the junction such that the valve leaflets are disposed inside the cavity.

Typically, valve frame 11 of valve 34B is shaped such that, when the valve is placed at junction 40, bulging portion 12 of frame 11 forms a cavity 42 that generates blood flow at the valve leaflets that is such as to prevent blood from stagnating in the vicinity of the valve leaflets. For some applications, the valve frame is shaped such that, when the valve is placed at junction 40, the bulging portion forms a cavity that is such as to cause blood flow in the vicinity of the downstream side of the valve leaflets to exert pressure on the valve leaflets, such that the valve leaflets close, or move closer together to facilitate closing. Alternatively, the valve frame is shaped such that, when the valve is placed at junction 40, the bulging portion forms a cavity that is such as to cause antegrade blood flow to accelerate in the vicinity of the downstream side of the valve leaflets, thereby causing (or enhancing) opening of the leaflets.

For some applications, valve 34B is configured to be retrieved from the renal vein, subsequent to being placed inside the renal vein. For some applications, valve 34B is retrieved by pulling the bulging portion 12 of frame 11, such as to cause the bulging portion to radially constrict.

Reference is now made to FIGS. 7A-D, which are schematic illustrations of a prosthetic valve 34C that is configured to be placed inside the subject's renal vein 32, a frame 50 of the valve being configured to cause the vein to form a bulged portion 52 around prosthetic valve leaflets 54 of the valve, in accordance with some applications of the present invention. Valve 34C is an example of prosthetic valve 34 described hereinabove with reference to FIGS. 4A-B.

Typically, valve 34C includes a frame 50 (e.g., a frame that is made of nitinol, stainless steel, cobalt chromium, platinum iridium (or other non-absorbable metals), magnesium (or other absorbable metals), a polymer, and/or a different material). Further typically, the valve includes prosthetic valve leaflets 54 (e.g., leaflets made from complete or partial venous valves harvested from calves, pigs, sheep, horses, marsupials, or other animals; leaflets made from pericardial tissue, from small intestinal submucosa from pigs or other animals, and/or from a synthetic material, such as polyester, polyurethane, any other polymer, and/or any thin and flexible material (e.g., material generated by electrospinning, or sputter deposition, including thin-film nitinol leaflets)). Still further typically, the valve includes sealing material 55, which is coupled to (e.g., sutured to) the valve frame, and that seals the valve frame with respect to the walls of the renal vein. For some applications, a similar material is used for sealing material 55 as is used for prosthetic valve leaflets 54. The frame supports the prosthetic valve leaflets, e.g., by the prosthetic valve leaflets being sutured to the frame. For some applications, the frame is shaped to define a generally cylindrical portion 56, the prosthetic valve leaflets being coupled to a downstream portion of the generally cylindrical portion. Valve 34C, as shown in FIGS. 7A-D, includes at least one protruding portion 58, which protrudes radially from the generally cylindrical portion of the valve frame. Typically, the protruding portion diverges radially from the cylindrical portion of the valve frame, such that the separation between the protruding portion and the cylindrical portion of the frame is greater at the downstream end of the protruding portion than at the upstream end of the protruding portion.

For some applications, the prosthetic valve is placed within a renal vein (e.g., within the main branch of the left renal vein, as shown), such that protruding portion 58 deforms at least a portion of the renal vein, such as to form bulged portion 52 within the renal vein. Typically, the prosthetic valve leaflets are coupled to the valve frame such that the valve leaflets are disposed at least partially (and typically, fully) downstream of the downstream end of the protruding portion. Thus, when the valve is placed within the renal vein, the valve leaflets are typically disposed within the bulged portion of the renal vein that is formed by the protruding portion. Typically, the valve frame is shaped such that, when the valve is placed within the renal vein, the protruding portion forms a bulged portion of the renal vein that generates blood flow at the valve leaflets that is such as to prevent blood from stagnating in the vicinity of the valve leaflets.

Figure 7B:
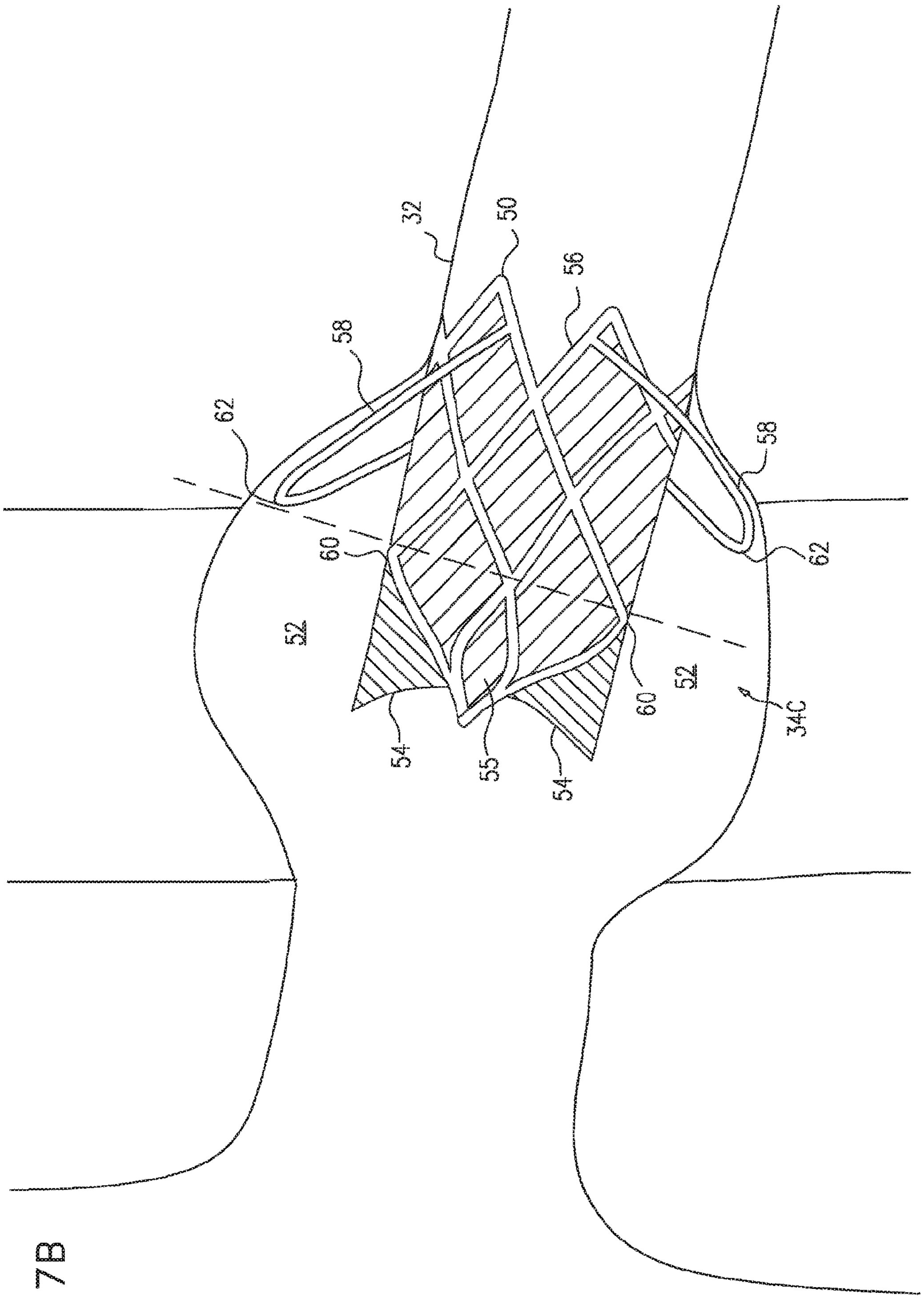
Figure 7C:
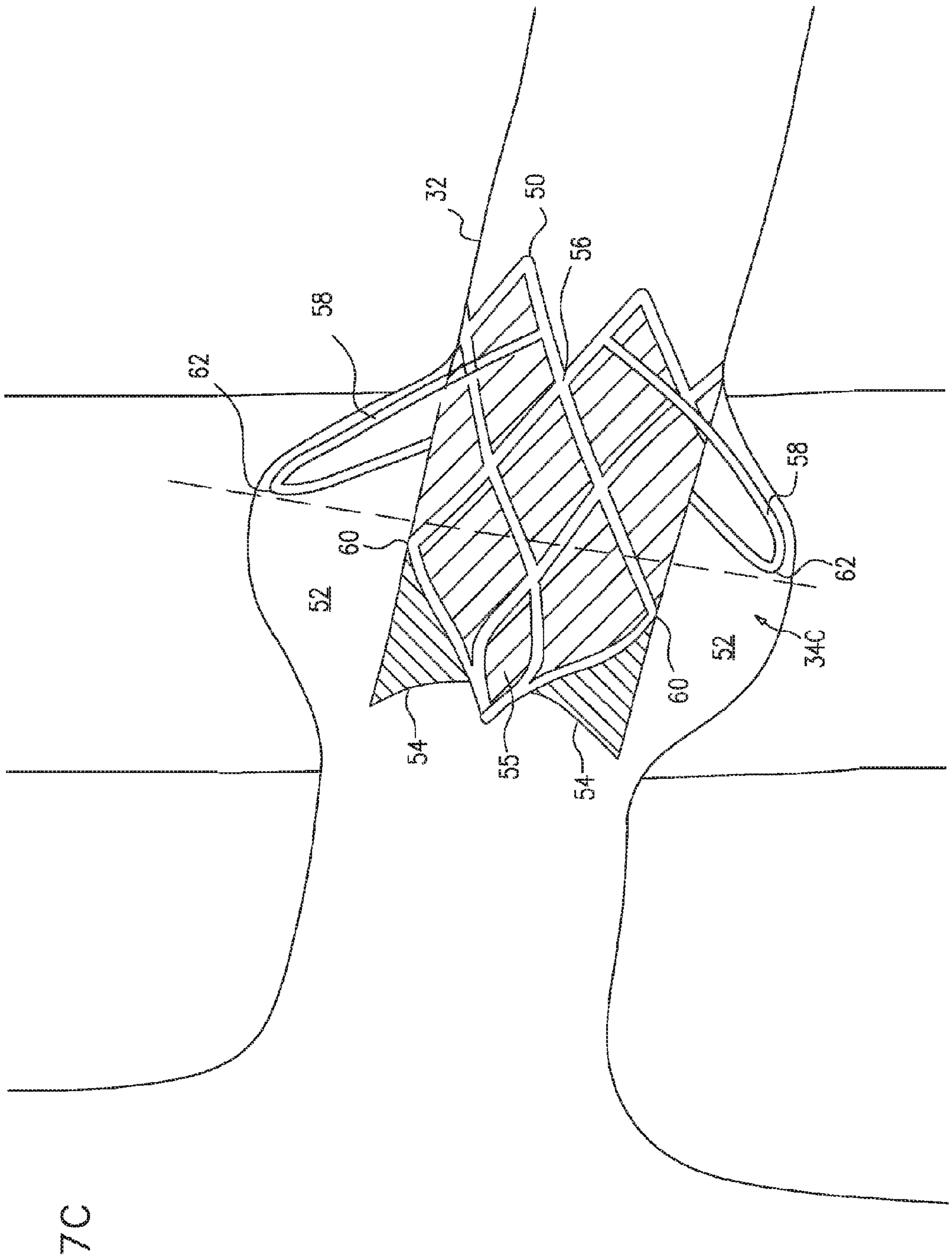
Figure 7D:
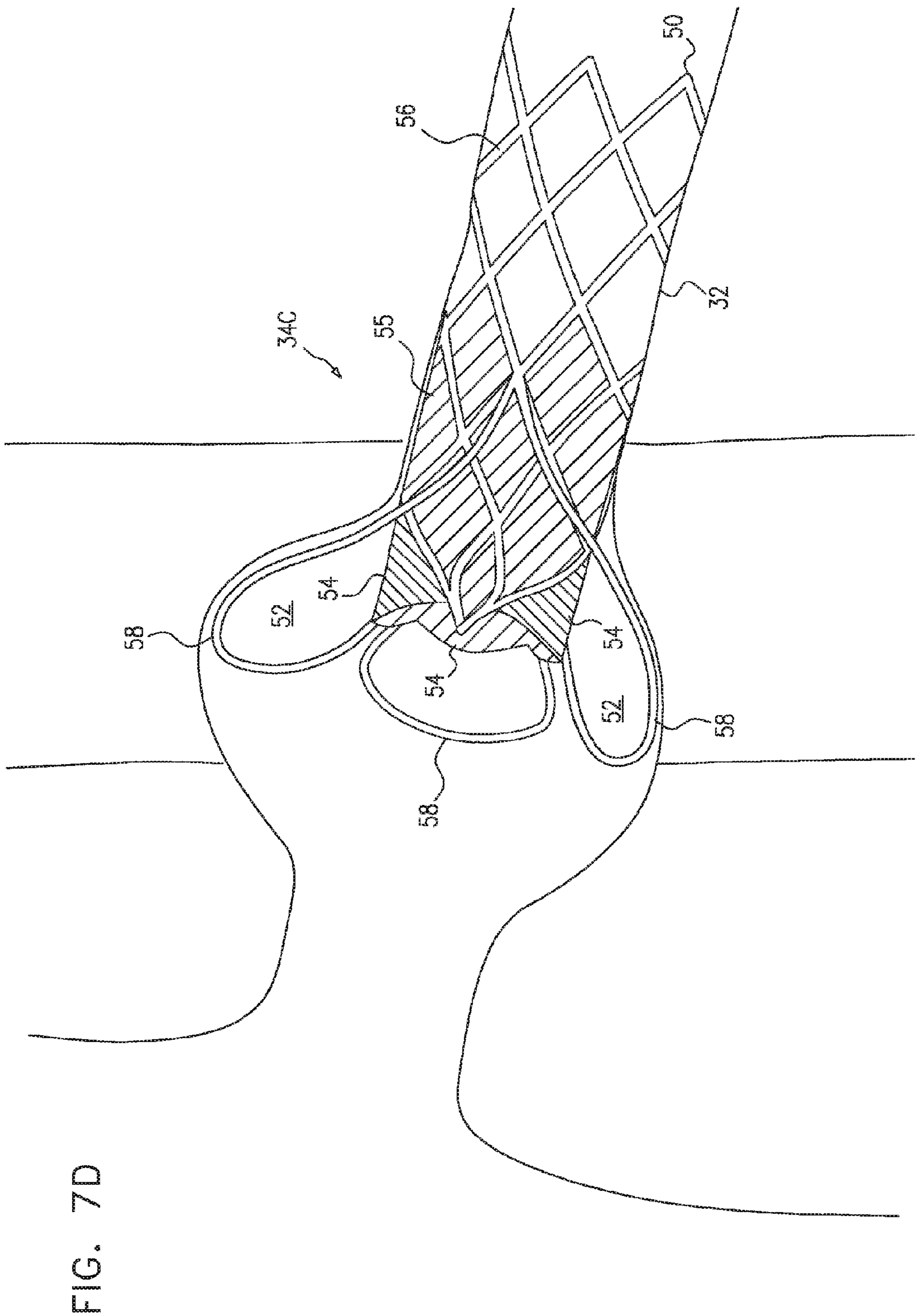

For some applications, the valve frame is shaped such that, when the valve is placed within the renal vein, the protruding portion forms a bulged portion of the renal vein that is such as to cause blood flow in the vicinity of the downstream side of the valve leaflets to exert pressure on the valve leaflets, such that the valve leaflets close, or move closer together to facilitate closing. For some applications, valve 34C is configured as shown in FIG. 7B or FIG. 7D, such that the bases of the valve leaflets are disposed within region of the bulged portion in which the vein is widening (e.g., in the vicinity of the region at which the bulged portion starts). For some such applications, the bulged portion causes vortex flow within the bulged portion, which exerts pressure on the downstream sides of the valve leaflets, such that the valve leaflets close. Alternatively, the valve frame is configured as shown in FIG. 7C, such that the bases of the valve leaflets are disposed in the vicinity of the region at which the cross sectional area of the bulged portion is at its maximum. For some such applications, the bulged portion causes antegrade blood flow to accelerate in the vicinity of the downstream side of the valve leaflets, thereby causing (or enhancing) opening of the leaflets.

For some applications, the bulged portion of the renal vein is such as to generate blood flow at the valve leaflets that is such as to prevent blood from stagnating in the vicinity of the valve leaflets.

Typically, prosthetic valve leaflets 54 are coupled to valve frame 50 such that an upstream end 60 of each of the prosthetic valve leaflets is longitudinally spaced from a downstream end 62 of the at least one protruding portion 58. This is shown in FIGS. 7B and 7C, which show that upstream ends 60 of each of the prosthetic valve leaflets are to the left (i.e., downstream) of the dashed line, whereas downstream ends 62 of the protruding portions 58 are to the right (i.e., upstream) of the dashed line. Thus, when the valve is placed within the renal vein, the valve leaflets are typically disposed within the bulged portion of the renal vein that is formed by the protruding portions, and the valve leaflets are not surrounded by any portion of the valve frame. Thus, even if the protruding portion is rigid or partially rigid, damage to the valve leaflets that may be caused, during opening of the valve leaflets, by the valve leaflets impacting the rigid or semi-rigid protruding portion, is prevented.

Alternatively, prosthetic valve leaflets 54 of valve 34C may be coupled to valve frame 50 such that an upstream end of each of the prosthetic valve leaflets is upstream of at least a portion of the at least one protruding portion 58. For some applications, protruding portions 58 are shaped and/or sized to be disposed outside of radial projections of downstream edges of the valve leaflets, such that when the prosthetic valve leaflets are fully opened, the leaflets do not impact any rigid or partially rigid portions of the protruding portions. For example, as shown in FIG. 7D, the protruding portion(s) may be shaped such that any rigid or partially rigid portions of the protruding portions are disposed around the outsides of the downstream edges of the prosthetic valve leaflets even when the valve leaflets are in fully-open states thereof. Thus, when the prosthetic leaflets are opened, the prosthetic leaflets may impact the vessel wall, but do not impact any rigid or partially rigid portions of the protruding portions.

For some applications, valve frame 50 defines a single protruding portion 58. For some applications, a single protruding portion is disposed around the full circumference of the valve frame. Alternatively, the valve frame defines two or more (e.g., two, three, or four) protruding portions that protrude from generally cylindrical portion 56 of the valve frame. Typically, the valve includes the same number of protruding portions as valve leaflets. For example, valve 34C as shown in FIG. 7D includes three protruding portions and three valve leaflets. The protruding portions deform the renal vein to form respective bulges in the vicinities of the protruding portions. For some applications, the bulges act in a generally similar manner to sinuses (such as the coronary sinus) that are naturally present in the human body in the vicinity of some native valves, the bulges enhancing blood flow in a vicinity of the valve leaflets such as to prevent blood from stagnating in the vicinity of the valve leaflets.

For some applications, valve frame 50 defines generally cylindrical portion 56, and at least one protruding portion 58 (e.g., a plurality of protruding portions), the generally cylindrical portion and the protruding portion being reversibly couplable to one another. Typically, the valve leaflets are coupled to the generally cylindrical portion, as described hereinabove. The at least one protruding portion is couplable to the cylindrical portion such that when the protruding portion is coupled to the cylindrical portion, the protruding portion protrudes radially from the cylindrical portion, as described hereinabove. For some applications, the protruding portion is implanted within the renal vein separately from the cylindrical portion. For example, the protruding portion may first be placed in the renal vein, and, subsequently, the cylindrical portion may be placed within the renal vein and coupled to the protruding portion.

For some applications of the invention, the valve leaflets of the prosthetic valve are replaced, subsequent to the valve having been placed in the subject's renal vein (e.g., in the event of fatigue of the valve leaflets). In order to replace the prosthetic valve leaflets, the cylindrical portion of the valve frame is decoupled from the protruding portion of the valve frame. The cylindrical portion is removed from the subject's body, and the protruding portion is left inside the subject's renal vein. Subsequently, a replacement cylindrical portion (or the same cylindrical portion with new prosthetic leaflets coupled thereto) is placed inside the renal vein and coupled to the protruding portion.

For some applications, valve frame 50 defines generally cylindrical portion 56, and at least one protruding portion 58 (e.g., a plurality of protruding portions), the cylindrical portion and the protruding portion being irreversibly coupled to one another, and/or being formed as a single integrated structure.

Figure 7E:
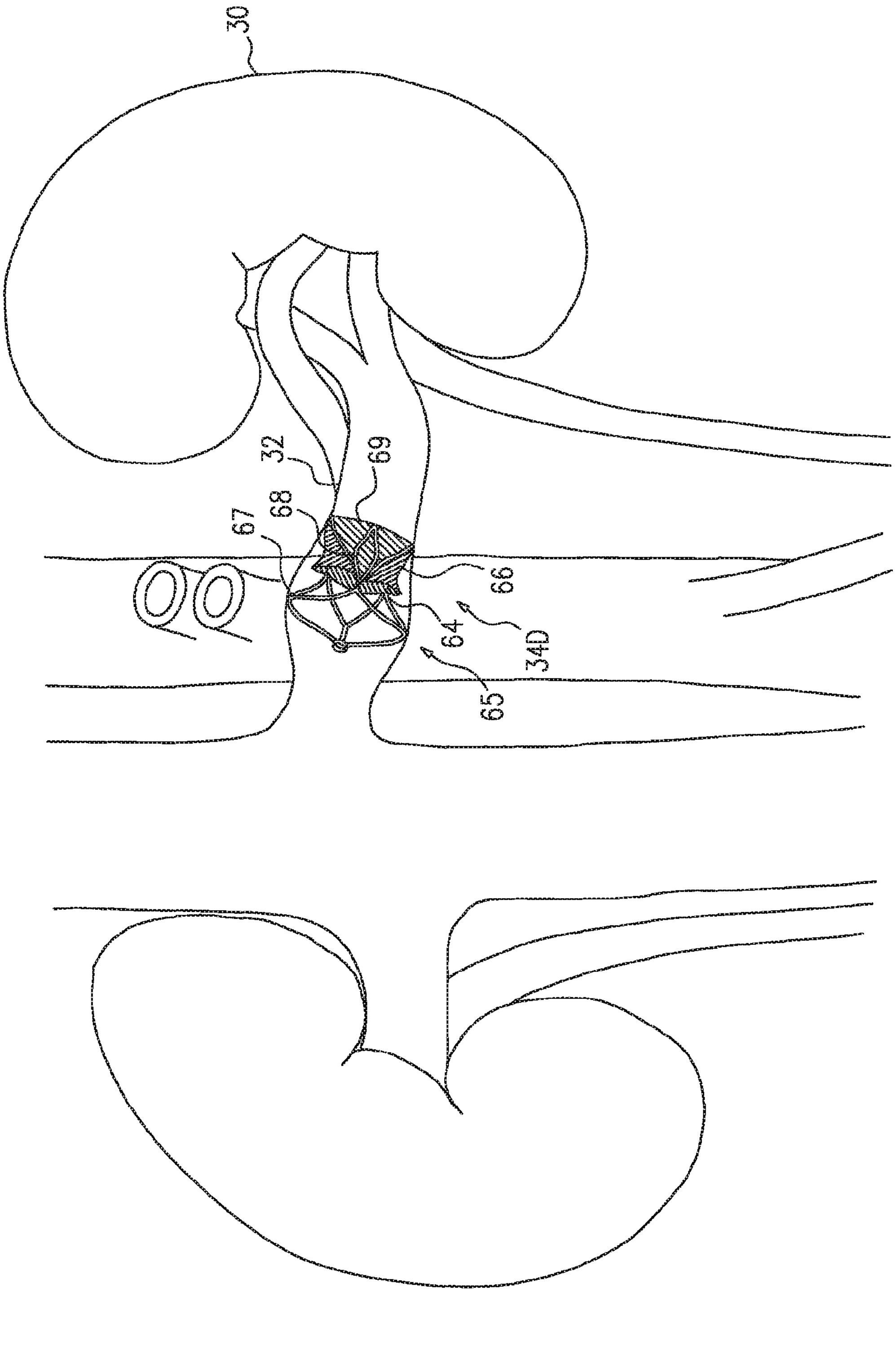
Figure 7F:
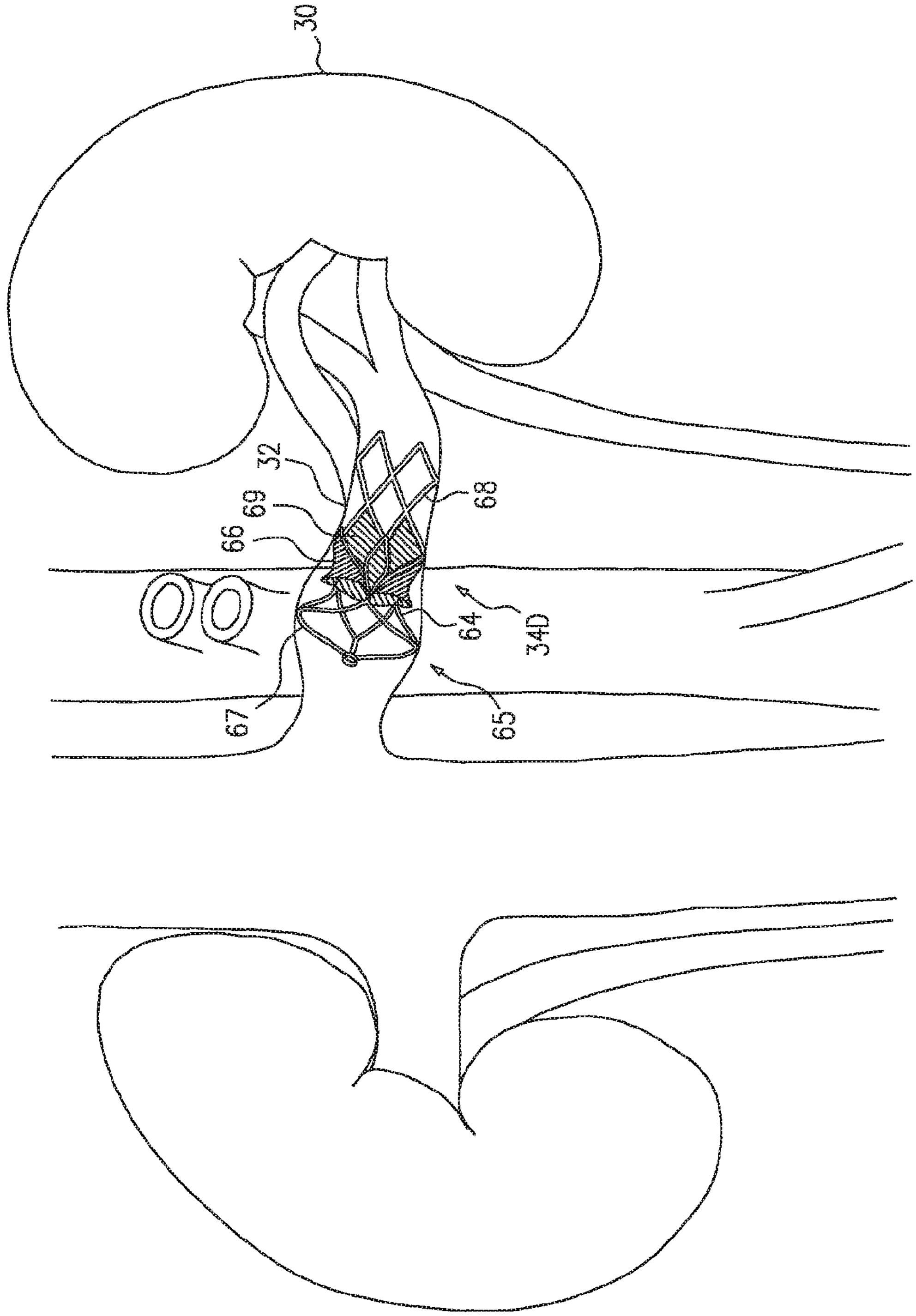

Reference is now made to FIGS. 7E-F, which are schematic illustrations of a prosthetic valve 34D that is configured to be placed inside the subject's renal vein 32, a frame 64 of the valve being configured to cause the vein to form a bulged portion 65 around prosthetic valve leaflets 66 of the valve, in accordance with some applications of the present invention. Valve 34D is an example of prosthetic valve 34 described hereinabove with reference to FIGS. 4A-B. Valve 34D is generally similar to valve 34C described with reference to FIGS. 7A-D, except that, rather than defining protruding portions that cause the vein to form bulged portions around the prosthetic valve leaflets (as described with reference to valve 34C, shown in FIGS. 7A-D), frame 64 of valve 34D is shaped to define a bulging portion 67 thereof that is configured to cause the vein to form bulged portions around prosthetic valve leaflets of the valve.

Typically, frame 64 of valve 34D includes a relatively narrow portion 68 thereof to which valve leaflets 66 are coupled. Further typically, a sealing material 69 is coupled to the narrow portion of the valve frame, the sealing material being configured to seal the valve frame with respect to the walls of the renal vein. The valve leaflets and the sealing material are generally as described hereinabove. Bulging portion 67 of frame 64 of valve 34D is typically disposed downstream with respect to the narrow portion of the valve frame and is bulged with respect to the narrow portion. Bulging portion 67 causes the renal vein to form a bulged portion, such that the valve leaflets are disposed inside the bulged portion. For some applications, the bulged portion is such as to cause vortex flow within the bulged portion, which exerts pressure on the downstream sides of the valve leaflets, such that the valve leaflets close. Alternatively or additionally, the bulged portion of the renal vein that is such as to cause antegrade blood flow to accelerate in the vicinity of the downstream side of the valve leaflets, thereby causing (or enhancing) opening of the leaflets. Further alternatively or additionally, the bulged portion of the renal vein is such as to generate blood flow at the valve leaflets that is such as to prevent blood from stagnating in the vicinity of the valve leaflets.

For some applications, frame 64 of valve 34D ends in the vicinity of the upstream ends of valve leaflets 66, as shown in FIG. 7E. Alternatively, the valve frame extends beyond the upstream ends of valve leaflets 66, such that when the valve is placed inside the renal vein the valve frame extends toward the subject's kidney 30.

For some applications, valve 34D is configured to be retrieved from the renal vein, subsequent to being placed inside the renal vein. For some applications, valve 34D is retrieved by pulling the bulging portion 67 of frame 64, such as to cause the bulging portion to radially constrict.

Figure 8:
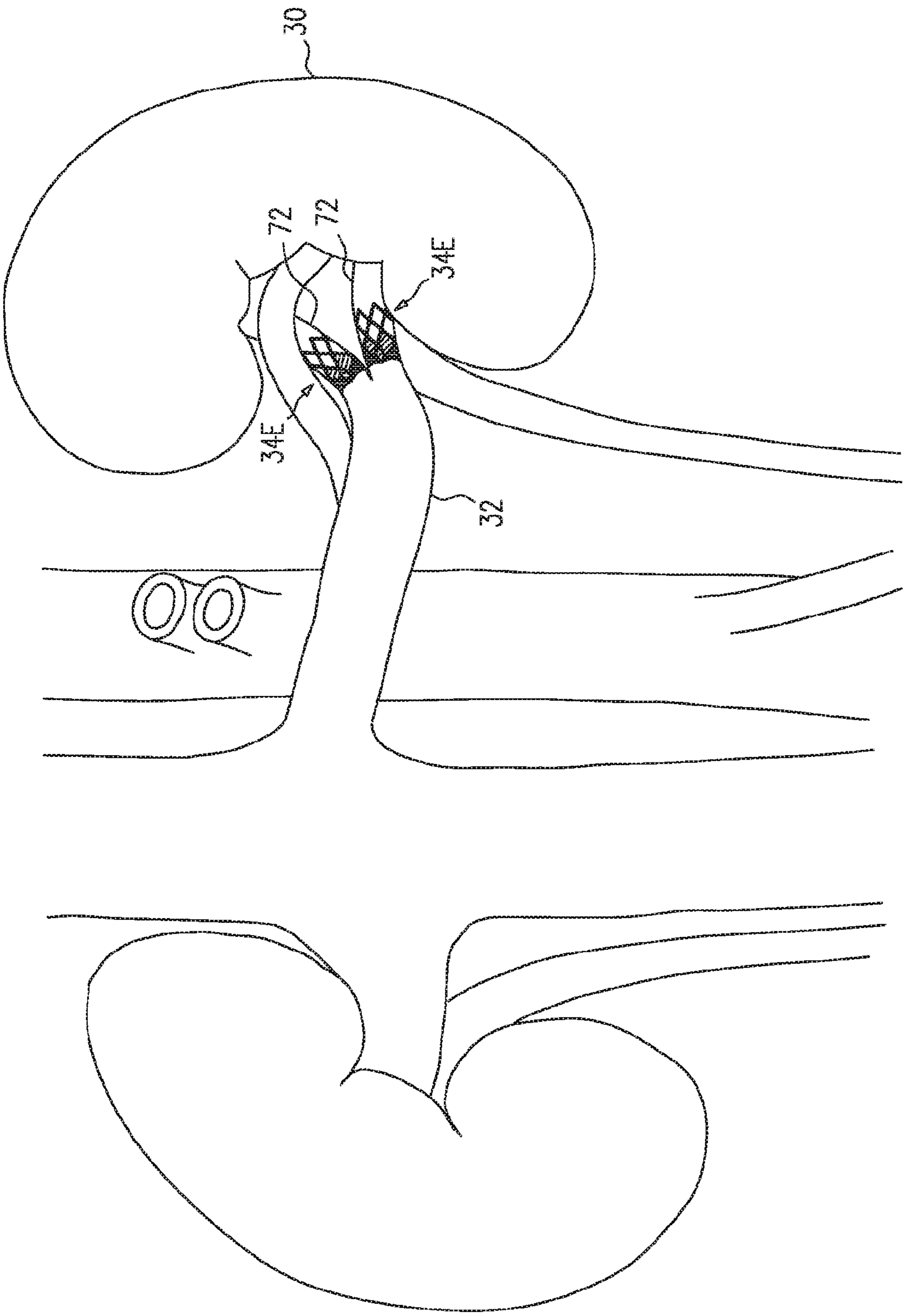
FIG. 8 is a schematic illustration of prosthetic valves that are placed within upstream branches of a subject's renal vein, in accordance with some applications of the present invention.

Reference is now made to FIG. 8, which is a schematic illustration of prosthetic valves 34E that are placed within upstream branches 72 of a subject's renal vein 32, in accordance with some applications of the present invention. Valve 34E is an example of prosthetic valve 34 described hereinabove with reference to FIGS. 4A-B. For some applications, prosthetic valve 34E is placed in one or more the upstream branches of the subject's left and/or right renal vein 32. The prosthetic valve is configured to reduce retrograde blood flow to the subject's kidney via the renal vein and/or to reduce renal venous pressure such that renal venous pressure is lower than the subject's central venous pressure, in a generally similar manner to that described hereinabove. For some applications, prosthetic valve 34E is generally similar to prosthetic valve 34C described hereinabove with reference to FIGS. 7A-D. Alternatively, valve 34E is generally similar to valve 34D described hereinabove with reference to FIG. 7E-F.

Figure 9:
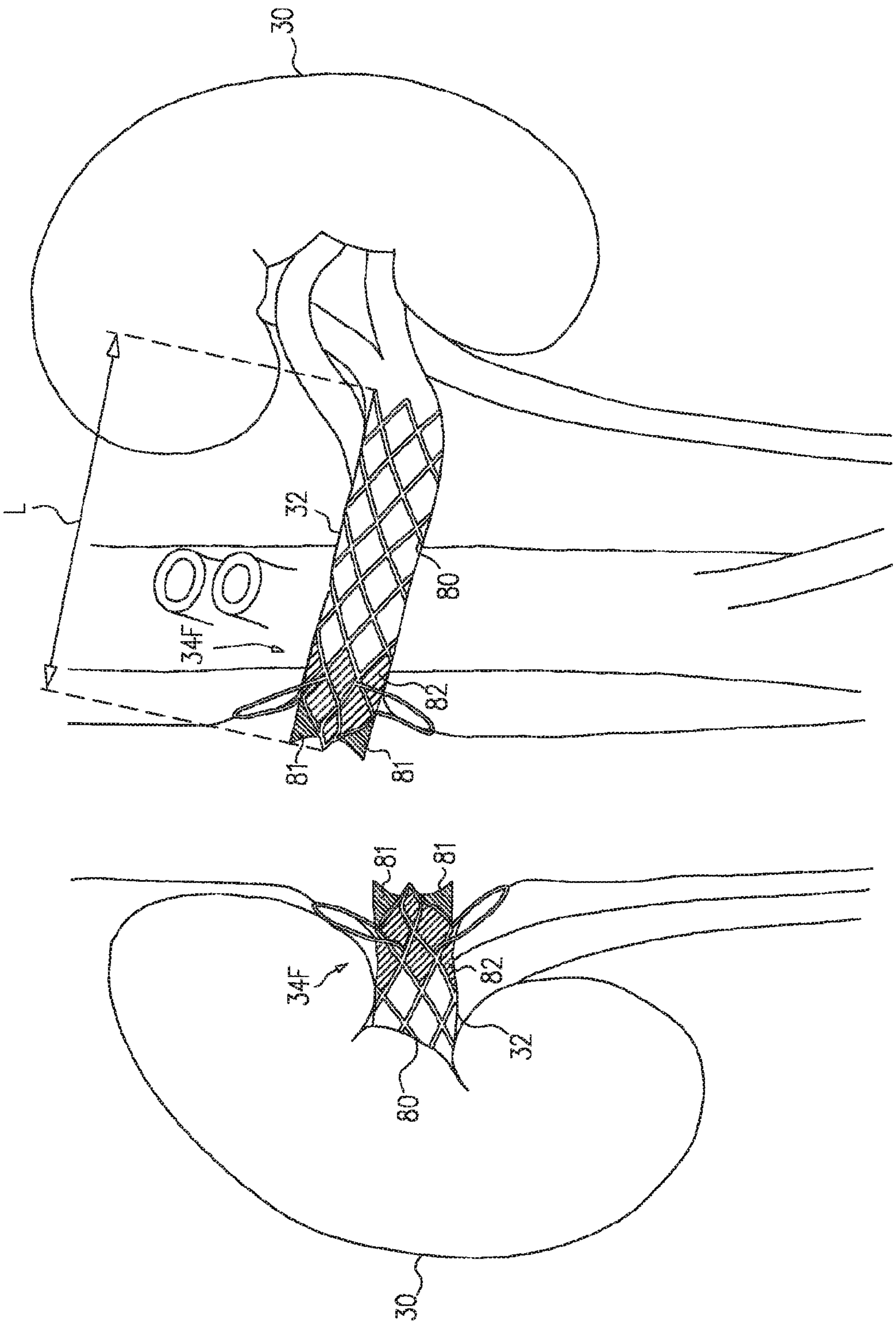
FIG. 9 is a schematic illustration of a prosthetic valve that includes an extended valve frame, the prosthetic valve being configured to be placed in a subject's renal vein such that the valve frame extends toward the subject's kidney, and reduces compression of the subject's renal vein resulting from intra-abdominal pressure, in accordance with some applications of the present invention.

Reference is now made to FIG. 9, which is a schematic illustration of a prosthetic valve 34F that includes an extended valve frame 80, the prosthetic valve being configured to be placed in a subject's renal vein 32 such that the valve frame extends toward the subject's kidney 30 and such that the valve frame reduces compression of the subject's renal vein resulting from intra-abdominal pressure, in accordance with some applications of the present invention. Valve 34F is an example of prosthetic valve 34 described hereinabove with reference to FIGS. 4A-B. Valve 34F typically includes valve leaflets 81 and sealing material 82 that are coupled to the valve frame. Typically, the valve leaflets and sealing material are generally as described hereinabove.

As shown, valve 34F is generally similar to valve 34A described hereinabove with reference to FIGS. 6A-C, except that valve 34F includes extended valve frame 80, such that when the valve is placed inside the renal vein the valve frame extends toward the subject's kidney 30. For some applications (not shown), valve 34F is generally similar to one of the other valves described hereinabove (e.g., valve 34B, valve 34C, valve 34D, or valve 34E) except that valve 34F includes extended valve frame 80, such that when the valve is placed inside the renal vein the valve frame extends toward the subject's kidney 30.

For some applications, prosthetic valve 34F is configured to reduce retrograde blood flow to the subject's kidney via the renal vein and/or to reduce renal venous pressure such that renal venous pressure is lower than the subject's central venous pressure, in a generally similar manner to that described hereinabove. Valve frame 80 of the prosthetic valve is typically rigid or semi-rigid. For applications in which valve 34F is configured to be placed in the subject's left renal vein, the valve frame typically has a length L of more than 20 mm (e.g., more than 25 mm), and/or less than 95 mm (e.g., less than 90 mm). For some applications, a ratio of the length of the valve to a maximum radial span of the valve is greater than 1:1, e.g., greater than 4:1. For applications in which valve 34F is configured to be placed in the subject's right renal vein, the valve frame typically has a length of more than 6 mm (e.g., more than 8 mm), and/or less than 45 mm (e.g., less than 40 mm). In addition to supporting prosthetic valve leaflets 81 of the prosthetic valve, the valve frame is configured to support the renal vein and to reduce (e.g., to prevent) compression of the renal vein that would occur in the absence of the valve frame, due to intra-abdominal pressure of the subject.

In general, the scope of the present invention includes placing a stent or a valve frame inside a subject's renal vein such as to protect the renal vein from compression due to high intra-abdominal pressure, resulting from fluid accumulation within the abdomen. For some applications, a valve that includes valve leaflets and a valve frame is placed inside the renal vein such that (a) the valve leaflets reduce retrograde blood flow to the subject's kidney via the renal vein, and/or reduce renal venous pressure such that renal venous pressure is lower than the subject's central venous pressure, and (b) the valve frame protects the renal vein from compression due to high intra-abdominal pressure, resulting from fluid accumulation within the abdomen.

Figure 10A:
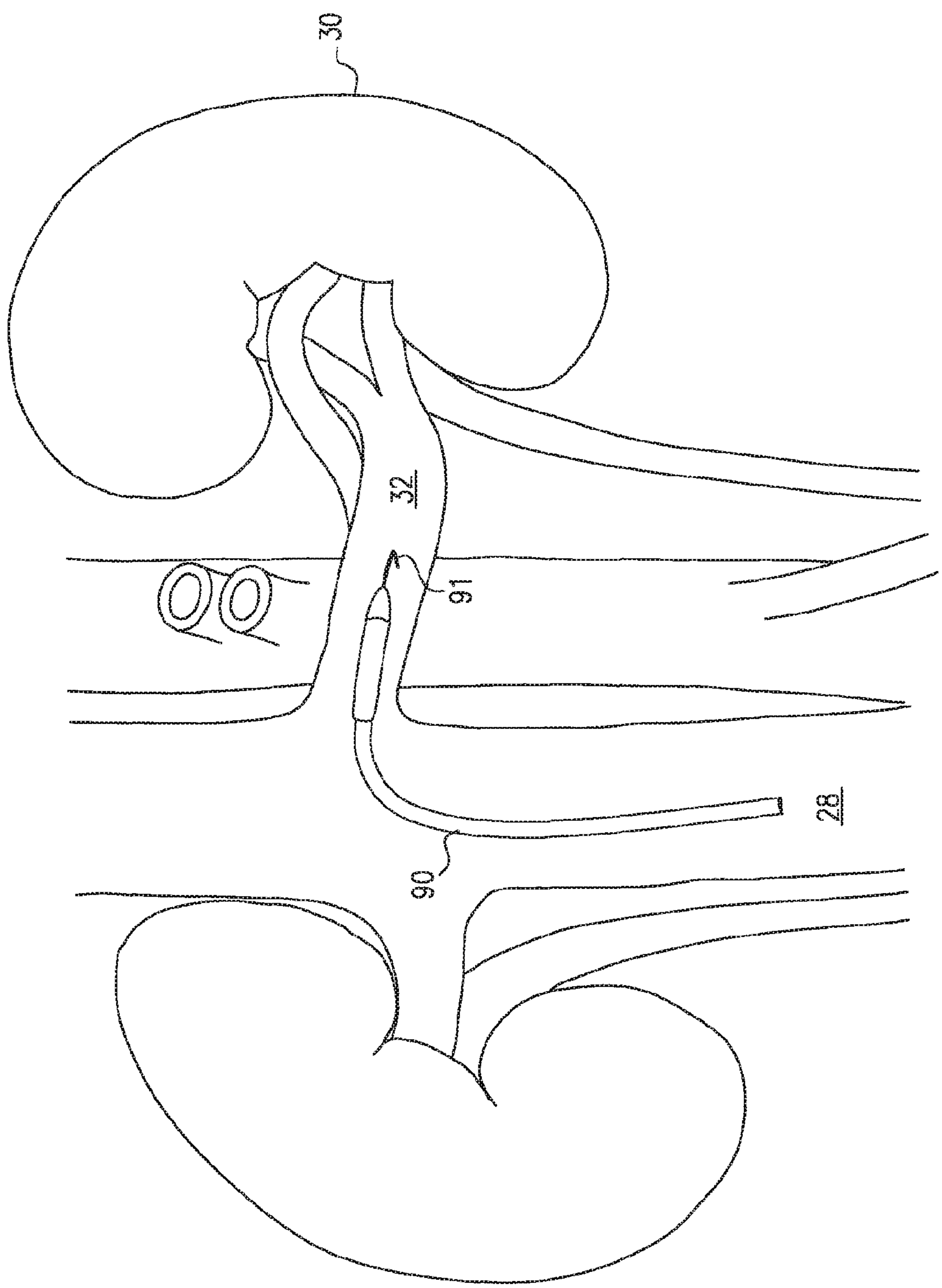
FIGS. 10A-D are schematic illustrations of a procedure for placing a prosthetic valve in a subject's renal vein, in accordance with some applications of the present invention.
Figure 10B:
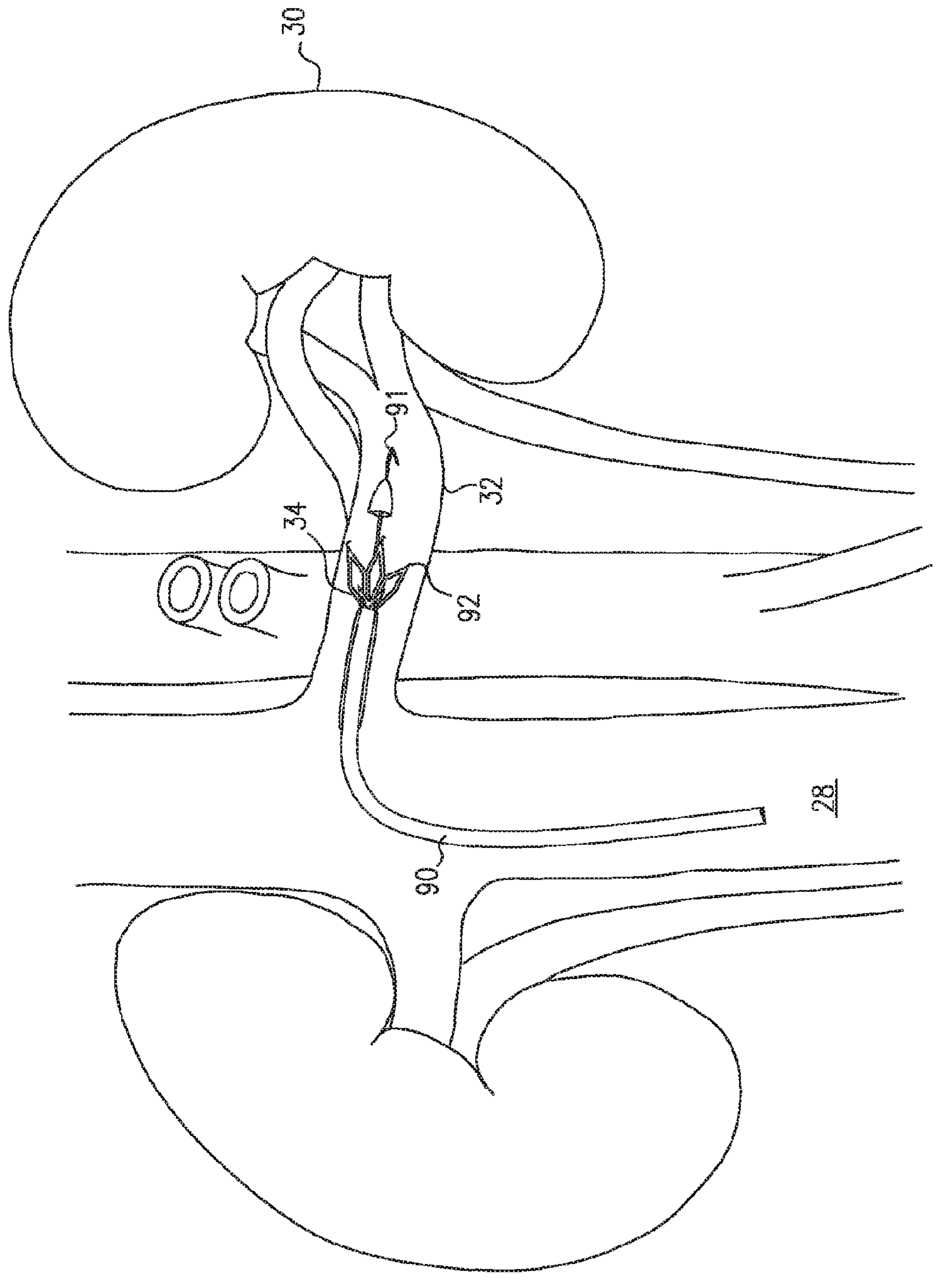

Reference is now made to FIGS. 10A-D, which are schematic illustrations of a procedure for placing a prosthetic valve 34 in a subject's renal vein 32, in accordance with some applications of the present invention. As shown in FIG. 10A, for some applications the valve is inserted into the renal vein via a catheter 90, e.g., via a transfemoral catheter that is advanced toward the renal vein via inferior vena cava 28. Typically the catheter is advanced over a guidewire 91. For some applications, when the distal end of the catheter is disposed inside the renal vein, the upstream end of the renal valve is advanced out of the distal end of the catheter, and/or the distal end of the catheter is retracted such as to release the upstream end of the renal valve from the catheter. Typically, the valve frame is configured to self expand upon being released from the catheter. Thus, in response to being advanced out of the distal end of the catheter, the upstream end of the valve expands such as to contact the wall of the renal vein, as shown in FIG. 10B. For some applications, prosthetic valve 34 defines barbs 92, or other coupling elements, that facilitate coupling of the valve to the wall of the renal vein.

Figure 10C:
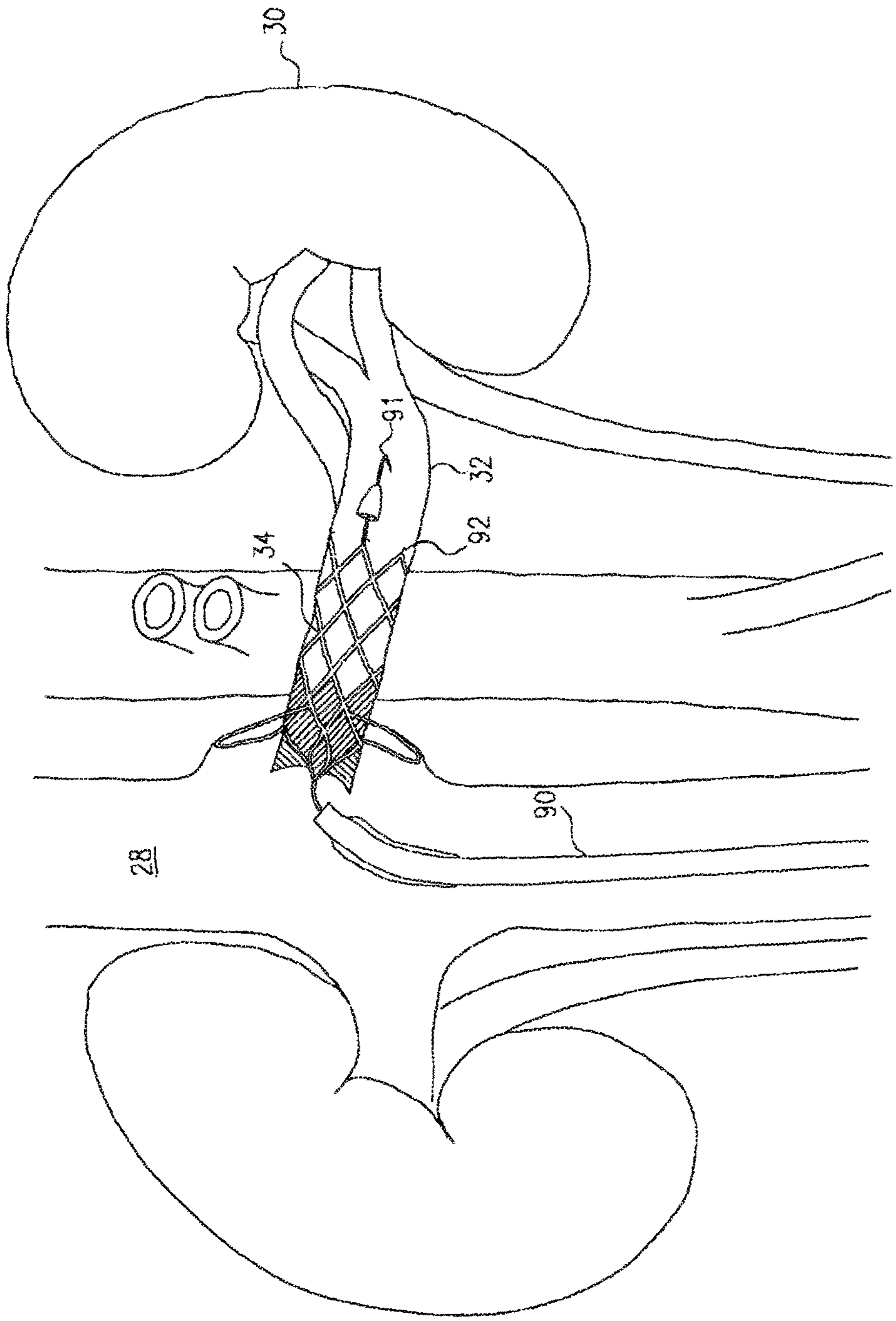
Figure 10D:
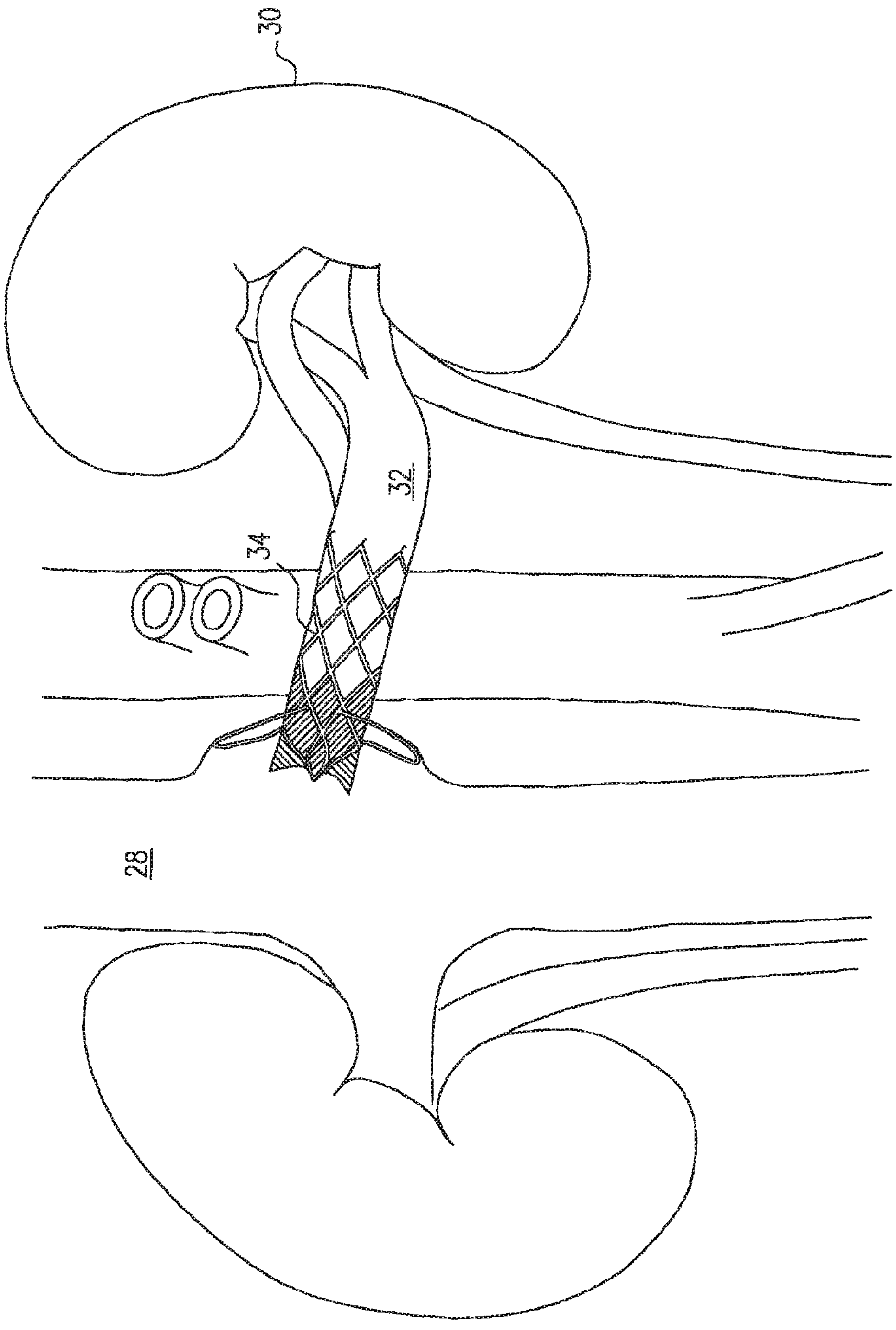

Subsequent to the coupling of the upstream end of valve 34 to the wall of renal vein 32, catheter 90 is retracted, such as to release the downstream end of the prosthetic valve. In response thereto, the downstream end of the valve typically self-expands, such as to contact the wall of the renal vein, e.g., such as to contact the wall of the renal vein at the junction of the renal vein with the vena cava, as shown in FIG. 10C. Subsequently, catheter 90 is fully retracted from the subject's body, leaving the prosthetic valve in place in the subject's renal vein, as shown in FIG. 10D.

It is noted that although the valve shown in FIGS. 10A-D appears generally similar to valve 34A described hereinabove with reference to FIGS. 6A-C, a generally similar implantation technique to that described with reference to FIGS. 10A-D may be used to implant any of the prosthetic valves described herein. It is further noted that, although according to the technique described with reference to FIGS. 10A-D, the upstream end of the valve is released from the catheter prior to the downstream end of the valve being released from the catheter, for some applications a generally similar implantation technique is used, but the downstream end of the valve is released from the catheter prior to the upstream end of the valve being released from the catheter, mutatis mutandis.

Reference is now made to FIG. 11, which is a schematic illustration of a valve 100 and a nozzle 102 disposed in a subject's vena cava 28, in accordance with some applications of the present invention. For some applications, as shown, the nozzle is formed from a stent 104 that is shaped as a nozzle and that has material 105 coupled thereto. Material 105 generally includes similar materials to those described hereinabove with reference to valve leaflets and sealing materials. The nozzle is coupled to the subject's vena cava at a location that is upstream of the junction of the vena cava with the right renal vein (and, typically, upstream of all of the junctions that the vena cava forms with the subject's renal veins). The nozzle is configured to direct antegrade blood flow through the vena cava past the subject's renal veins and to thereby protect the renal veins from flow and pressure of blood from the portion of the vena cava that is upstream of the renal veins.

Valve 100 is coupled to the subject's vena cava at a location that is downstream of the junction of the vena cava with the left renal vein (and, typically, downstream of all of the junctions that the vena cava forms with the subject's renal veins). Valve 100 typically includes a valve frame 106, valve leaflets 107, and sealing material 108. The valve leaflets and the sealing material are coupled to the valve frame, and are typically generally similar to the valve leaflets and the sealing materials described hereinabove. The valve leaflets are configured to (a) open in response to antegrade blood flow through the vena cava from a location within the vena cava that is upstream of the valve leaflets to a location within the vena cava that is downstream of the valve leaflets, and (b) close in response to retrograde blood flow through the vena cava from a location within the vena cava that is downstream of the valve leaflets to a location within the vena cava that is upstream of the valve leaflets. Thus valve 100 is configured to prevent the renal veins from backflow and pressure of blood from the portion of the vena cava that is downstream of the renal veins.

Figure 12A:
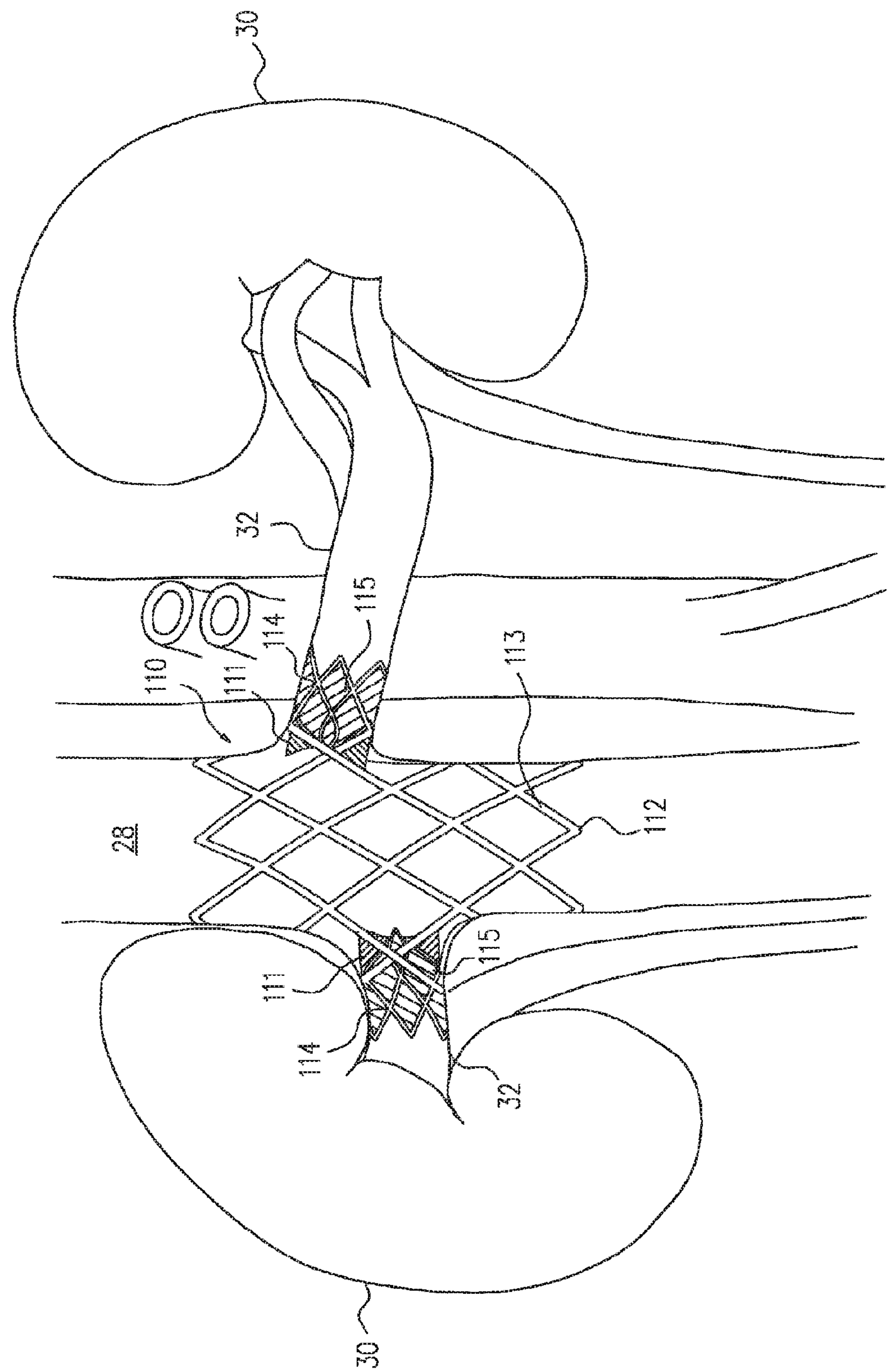
FIGS. 12A-B are schematic illustrations of a valve disposed in a subject's vena cava, leaflets of the valve being coupled to a frame of the valve, such that the valve leaflets are disposed in the vicinity of ostia at the junction of the renal vein with the vena cava, in accordance with some applications of the present invention.

Reference is now made to FIG. 12A, which is a schematic illustration of a valve 110 disposed in a subject's vena cava 28, leaflets 111 of the valve being coupled to a frame 112 of the valve, such that the valve leaflets are disposed in the vicinity of the ostia at the junctions of the renal veins 32 with the vena cava 28, in accordance with some applications of the present invention. Valve frame 112 is shaped to define a central portion 113 and side branches 114. Typically, the central portion and side branches are a single integrated structure. Alternatively the side branches are formed separately from the central portion and are coupled to the central portion. For example, the side branches may be coupled to the central portion inside the subject's body, or before being placed inside the subject's body. The central portion is configured to be disposed in the vena cava and the side branches are configured to be disposed in respective renal veins of the subject. Valve leaflets 111 are coupled to the valve frame (e.g., to the side branches of the valve frame) such that the valve leaflets are disposed inside the subject's renal veins in vicinities of the ostia at the junctions of the renal veins 32 with the vena cava 28. The valve leaflets are configured to open in response to antegrade blood flow from the renal vein into the vena cava and to close in response to retrograde flow from the vena cava into the renal vein. Typically, sealing material 115 is coupled to the valve frame and is configured to seal the valve frame with respect to the walls of the renal veins.

Figure 12B:
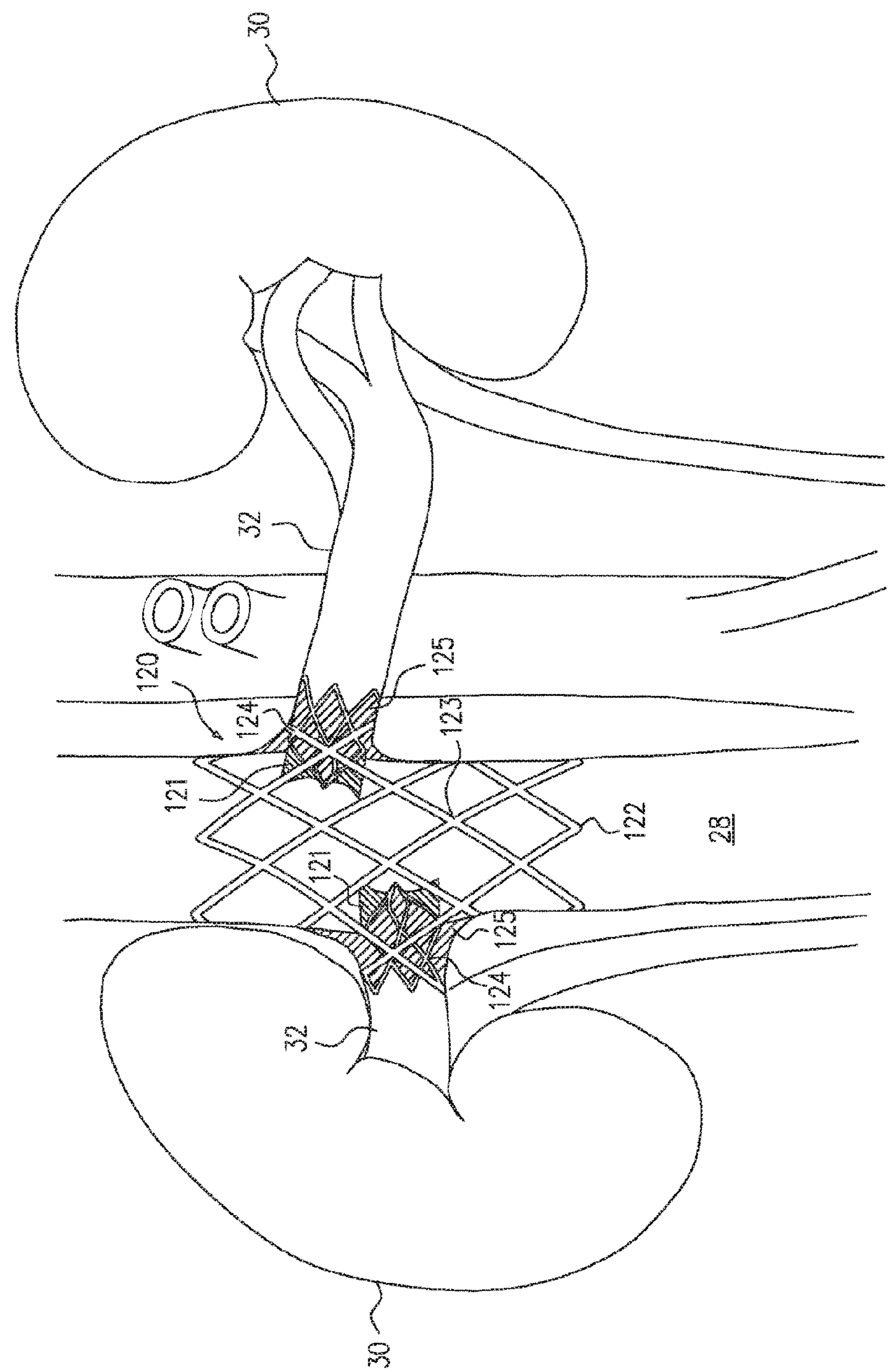

Reference is now made to FIG. 12B, which is a schematic illustration of a valve 120 disposed in a subject's vena cava 28, leaflets 121 of the valve being coupled to a frame 122 of the valve, such that the valve leaflets are disposed in the vicinity of the ostia at the junctions of the renal veins 32 with the vena cava 28, in accordance with some applications of the present invention. Valve 120 is generally similar to valve 110 described with reference to FIG. 12A, except that valve leaflets 121 of valve 120 are coupled to the valve frame such that the valve leaflets are disposed inside the subject's vena cava, rather than being disposed inside the subject's renal veins. Typically, the valve leaflets are configured to be disposed inside the vena cava in vicinities of the ostia at the junctions of the renal veins 32 with the vena cava 28. The valve leaflets are configured to open in response to antegrade blood flow from the renal vein into the vena cava and to close in response to retrograde flow from the vena cava into the renal vein. Valve frame 122 is shaped to define a central portion 123 and side branches 124. Typically, the central portion and side branches are a single integrated structure. Alternatively the side branches are formed separately from the central portion and are coupled to the central portion. For example, the side branches may be coupled to the central portion inside the subject's body, or before being placed inside the subject's body. The central portion is configured to be disposed in the vena cava and the side branches are configured to be disposed in respective renal veins of the subject. Typically sealing material 125 is coupled to the valve frame and is configured to seal the valve frame with respect to the walls of the renal veins.

It is noted that, although a prosthetic valve that defines a valve frame and prosthetic valve leaflets has been described as being used to reduce and/or prevent retrograde blood flow to a subject's kidney, and/or to reduce renal venous pressure relative to central venous pressure, for some applications, a different device is used to reduce and/or prevent retrograde blood flow to the subject's kidney, and/or to reduce renal venous pressure relative to central venous pressure. For some applications, an electronically-controlled valve or shutter is used, the valve or shutter being configured to be opened and closed in response to physiological signals of the subject that are detected using a sensor (e.g., an ECG sensor, and/or a blood pressure sensor). For some applications, an active micro-assist device, such as an archimedes screw, is used to reduce and/or prevent retrograde blood flow to a subject's kidney, to reduce renal venous pressure relative to central venous pressure, and/or to promote antegrade blood flow from the renal vein to the vena cava. For some applications, a stent is placed in the renal vein such as to reduce pressure in the renal vein relative to pressure in the renal vein in the absence of the stent, by reducing compression of the subject's renal vein resulting from intra-abdominal pressure of the subject.

It is further noted that the scope of the present invention includes using a bi-leaflet valve, a tri-leaflet valve, or a valve having any number of leaflets for any of the valves described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with renal veins and a vena cava of a subject, the method comprising:

identifying the subject as suffering from a condition that causes the subject to have elevated central venous pressure; and in response thereto, reducing blood pressure within the subject's renal veins relative to the subject's central venous pressure, by directing antegrade blood flow through the subject's vena cava past the subject's renal veins, by placing a nozzle inside the subject's vena cava, such that an upstream end of the nozzle is placed at a location upstream of junctions of the vena cava with one or more of the subject's renal veins, the nozzle converging from the upstream end of the nozzle to a downstream end of the nozzle.

2. The method according to claim 1, further comprising placing an additional device within the vena cava at a location that is downstream of the junctions of the vena cava with one or more of the subject's renal veins, the additional device being configured to direct blood flow through the vena cava in an antegrade direction.

3. The method according to claim 2, wherein placing the additional device within the vena cava downstream of the junctions of the vena cava with one or more of the subject's renal veins comprises placing a valve inside the subject's vena cava at the location that is downstream of the junctions of the vena cava with one or more the subject's renal veins, the valve being configured to allow antegrade blood flow therethrough and to prevent retrograde blood flow therethrough.

4. A method for use with renal veins and a vena cava of a subject, the method comprising:

identifying a subject as suffering from a condition that causes the subject to have elevated central venous pressure; and in response thereto, placing a device inside the vena cava such that an upstream end of the device is placed at a location upstream of junctions of the vena cava with one or more of the subject's renal veins, the device defining a passage through the device, at least a portion of the passage converging in a direction from the upstream end of the device to downstream end of the device.

5. The method according to claim 4, wherein placing the device inside the vena cava such that the upstream end of the device is placed at the location upstream of junctions of the vena cava with one or more of the subject's renal veins comprises placing a nozzle inside the vena cava such that an upstream end of the nozzle is placed at the location upstream of junctions of the vena cava with one or more of the subject's renal veins.

6. The method according to claim 4, further comprising placing an additional device within the vena cava at a location that is downstream of the junctions of the vena cava with one or more of the subject's renal veins, the additional device being configured to direct blood flow through the vena cava in an antegrade direction.

7. The method according to claim 6, wherein placing the device inside the vena cava such that the upstream end of the device is placed at the location upstream of junctions of the vena cava with one or more of the subject's renal veins comprises placing a nozzle inside the vena cava such that the upstream end of the device is placed at the location upstream of junctions of the vena cava with one or more of the subject's renal veins.

8. The method according to claim 6, wherein placing the additional device within the vena cava downstream of the junctions of the vena cava with one or more of the subject's renal veins comprises placing a valve inside the subject's vena cava at the location that is downstream of the junctions of the vena cava with the subject's renal veins, the valve being configured to allow antegrade blood flow therethrough and to prevent retrograde blood flow therethrough.

9. The method according to claim 8, wherein placing the device inside the vena cava such that the upstream end of the device is placed at the location upstream of junctions of the vena cava with one or more of the subject's renal veins comprises placing a nozzle inside the vena cava such that the upstream end of the device is placed at the location upstream of junctions of the vena cava with one or more of the subject's renal veins.

* * * * *